(12) United States Patent
Fässler et al.

(10) Patent No.: US 6,225,345 B1
(45) Date of Patent: May 1, 2001

(54) AZAHEXANE DERIVATIVES AS SUBSTRATE ISOSTERS OF RETROVIRAL ASPARATE PROTEASES

(75) Inventors: Alexander Fässler, Macclesfield (GB); Guido Bold, Gipf-Oberfrick; Hans-Georg Capraro, Rheinfelden, both of (CH); Marc Lang, Mulhouse (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/068,876

(22) PCT Filed: Nov. 13, 1996

(86) PCT No.: PCT/EP96/04968

§ 371 Date: May 21, 1998

§ 102(e) Date: May 21, 1998

(87) PCT Pub. No.: WO97/19055

PCT Pub. Date: May 29, 1997

(30) Foreign Application Priority Data

Nov. 21, 1995 (CH) ........................................ 3296/95
Jul. 5, 1996 (CH) .................................... 1686/96

(51) Int. Cl.[7] ........................ A61K 31/27; C07C 271/10; C07C 269/04
(52) U.S. Cl. ........................ 514/483; 514/934; 558/417; 560/25; 560/26
(58) Field of Search ............................. 558/417; 560/25, 560/26; 514/519, 520, 521, 522, 538, 539, 683, 934

(56) References Cited

FOREIGN PATENT DOCUMENTS

| | | |
|---|---|---|
| 0 337 714 | 10/1989 | (EP) . |
| 0 521 827 | 1/1993 | (EP) . |
| 0 604 368 | 6/1994 | (EP) . |
| 0 615 969 | 9/1994 | (EP) . |
| WO 94 19332 | 9/1994 | (WO) . |

OTHER PUBLICATIONS

S.D. Young, et al., *Journal of Medicinal Chemistry*, vol. 35, No. 10, p. 1704 (1992).

*Primary Examiner*—Shailendra Kumar
(74) *Attorney, Agent, or Firm*—Thomas Hoxie; Ellen K. Park

(57) ABSTRACT

The invention relates to compounds of formula (I):

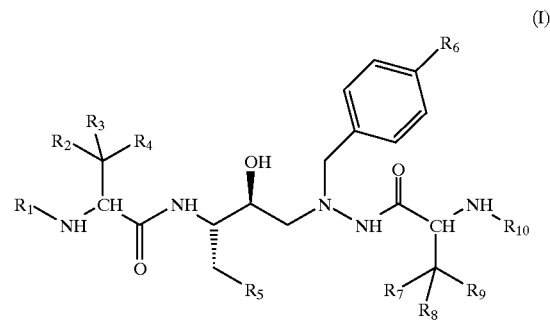

wherein $R_1$ and $R_{10}$ are each independently of the other lower alkoxycarbonyl; either $R_2$, $R_3$ and $R_4$ are each independently of the other $C_1$–$C_4$alkyl and $R_7$, $R_8$ and $R_9$ are each selected from hydrogen and $C_1$–$C_4$alkyl, with not more than 2 of the radicals being hydrogen; or $R_7$, $R_8$ and $R_9$ are each independently of the other $C_1$–$C_4$alkyl and $R_2$, $R_3$ and $R_4$ are each selected from hydrogen and $C_1$–$C_4$alkyl, with 1 or 2 of the radicals being hydrogen; $R_5$ is phenyl or cyclohexyl; and $R_6$ is phenyl or cyanophenyl; or salts thereof; those compounds are inhibitors of retroviral aspartate proteases and are effective, for example, against HIV.

15 Claims, No Drawings

AZAHEXANE DERIVATIVES AS SUBSTRATE ISOSTERS OF RETROVIRAL ASPARATE PROTEASES

This application is a 371 of PCT/EP96/04968, filed Nov. 13, 1996.

BRIEF DESCRIPTION OF THE INVENTION

The invention relates to azahexane derivatives having the property of being substrate isosteres of retroviral aspartate proteases, to salts thereof, to processes for the preparation of those compounds and their salts, to pharmaceutical compositions comprising those compounds or their salts, and to the use of those compounds or their salts (alone or in combination with other antiretrovirally active compounds) in the therapeutic or diagnostic treatment of the human or animal body or in the preparation of pharmaceutical compositions.

BACKGROUND TO THE INVENTION

According to WHO estimates there are clearly more than 20 million people infected by HIV-1 or HIV-2. Sooner or later that infection manifests itself by way of preliminary stages, such as ARDS, in a manifest disease of the immune system which is known as "Acquired Immunodeficiency Syndrome" or AIDS. In the overwhelming number of cases the disease sooner or later leads to the death of the infected patients.

Hitherto, the treatment of retroviral diseases, such as AIDS, has involved principally the use of inhibitors of reverse transcriptase, an enzyme effective in the conversion of retroviral RNA into DNA, such as 3'-azido-3'-deoxythymidine (AZT) or dideoxyinosine (DDI), and also trisodium phosphonoformate, ammonium-21-tungstenato-9-antimonate, 1-β-D-ribofuranoxyl-1,2,4-triazole-3-carboxamide and dideoxycytidine and also adriamycin. Attempts have also been made to introduce into the body, for example in the form of a recombinant molecule or molecule fragment, the T4-cell receptor which is present in certain cells of the defence system of the human body and is responsible for the anchoring and introduction of infectious virus particles into those cells and thus for their infection, the objective being that binding sites for the virus will be blocked so that the virions will no longer be able to bind to the cells. Compounds that prevent the virus penetrating the cell membrane in some other way, such as polymannoacetate, are also used.

Also reported are advanced clinical experiments with a hydroxyethylene isostere as an inhibitor of HIV-protease, N-tert-butyl-decahydro-2-[2(R)-hydroxy-4-phenyl-3(S)-[[N-2-quinolyl-carbonyl-L-asparaginyl]amino]butyl]-(4aS, 8aS)-isoquinoline-3(S)-carboxamide (Ro 31-8959). That compound exhibits an inhibitory action against HIV-protease in vitro, suppression of virus replication in cell experiments and, in experiments on rodents, blood levels that are still usable are achieved even in the case of oral administration (see Roberts, N. A., et al., Biochemical Soc. Transactions 20, 513–516 (1992)); usable blood levels have also been achieved in humans (see e.g. G. J. Muirhead et al., Brit. J. Clin. Pharmacol. 34, 170P–171 P (1992)). A so-called "surrogate-marker" (titre of the CD4-lymphocytes in the blood, the decrease in which in untreated patients is a measure of the advance of the AIDS disease) has shown initial positive effects in AIDS patients (see "Roche Statement on HIV Proteinase Inhibitor (Ro 31-8959) European Trials Results", distributed to participants in the 9th International Congress on AIDS in Berlin, Jun. 7–11, 1993). A disadvantage of that compound, Ro 31-8959, is that it is expensive to synthesise.

Also under development are a number of further inhibitors of retroviral aspartate protease, an enzyme the function of which can be characterised as follows:

In the AIDS viruses, HIV-1 and HIV-2, and other retroviruses, for example corresponding viruses in cats (FIV) and apes (SIV), the proteolytic maturation of, for example, the core proteins of the virus is brought about by an aspartate protease, such as HIV-protease. Without that proteolytic maturation, infectious virus particles cannot be formed. Owing to the central role of the said aspartate proteases, such as HIV-1- or HIV-2-protease, in the maturation of viruses and on the basis of experimental results, for example on infected cell cultures, it has become plausible that effective suppression of the maturation step brought about by that protease will suppress the assembly of mature virions in vivo. Corresponding inhibitors can therefore be used therapeutically.

The aim of the present invention is to provide a novel type of compound that is equipped, especially, with a high degree of inhibitory activity against virus replication in cells, high anti-viral activity against numerous virus strains, including those which are resistant to known compounds, such as saquinavir and indinavir, and especially advantageous pharmacological properties, for example good pharmacokinetics, such as high bioavailabilty and high blood levels, and/or high selectivity.

FULL DESCRIPTION OF THE INVENTION

The azahexane derivatives according to the invention are compounds of formula I

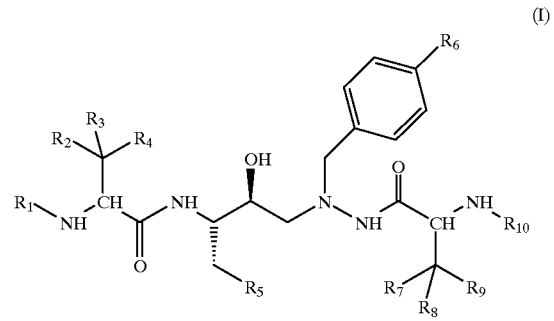

wherein $R_1$ and $R_{10}$ are each independently of the other lower alkoxycarbonyl;

either $R_2$, $R_3$ and $R_4$ are each independently of the other $C_1$–$C_4$alkyl and $R_7$, $R_8$ and $R_9$ are each selected from hydrogen and $C_1$–$C_4$alkyl, with not more than 2 of the radicals being hydrogen;

or $R_7$, $R_8$ and $R_9$ are each independently of the other $C_1$–$C_4$alkyl and $R_2$, $R_3$ and $R_4$ are each selected from hydrogen and $C_1$–$C_4$alkyl, with 1 or 2 of the radicals being hydrogen;

$R_5$ is phenyl or cyclohexyl; and $R_6$ is phenyl or cyanophenyl;

or salts thereof.

Those compounds exhibit unexpectedly good and surprisingly positive pharmacological properties, as indicated in detail below, and are relatively simple to synthesise.

Unless indicated to the contrary, the general terms used hereinabove and hereinbelow preferably have the following meanings within the scope of this disclosure:

The term "lower" indicates a radical having up to and including a maximum of 7 carbon atoms, preferably up to and including a maximum of 4 carbon atoms, the radicals in question being unbranched or branched one or more times.

Lower alkyl and $C_1$–$C_4$alkyl are especially tert-butyl, sec-butyl, isobutyl, n-butyl, isopropyl, n-propyl, ethyl and especially methyl.

Any reference to compounds, salts and the like in the plural also includes a compound, a salt and the like.

Any asymmetric carbon atoms present, for example the carbon atoms bonded to the radicals $R_2$, $R_3$ and $R_4$ and to $R_7$, $R_8$ and $R_9$ and the carbon atoms carrying the radical [($R_2$)($R_3$)($R_4$)C]— or [($R_7$)($R_8$)($R_9$)C]— in compounds of formula I, may be in the (R)-, (S)- or (R,S)-configuration, preferably in the (R)- or (S)-configuration, the (S)-configuration being especially preferred in the case of the carbon atoms carrying the radical [($R_2$)($R_3$)($R_4$)C]— or [($R_7$)($R_8$)($R_9$)C]— in compounds of formula I. Accordingly, the compounds in question may be in the form of isomeric mixtures or in the form of pure isomers, preferably in the form of pure diastereoisomers.

Lower alkoxycarbonyl is preferably $C_1$–$C_4$alkoxycarbonyl wherein the alkyl radical may be branched or unbranched, and is especially ethoxycarbonyl or more especially methoxycarbonyl.

As $R_5$, phenyl is preferred to cyclohexyl.

Cyanophenyl is preferably 4-, 3- or especially 2-cyanophenyl.

The compounds of formula I preferably have the formula Ia

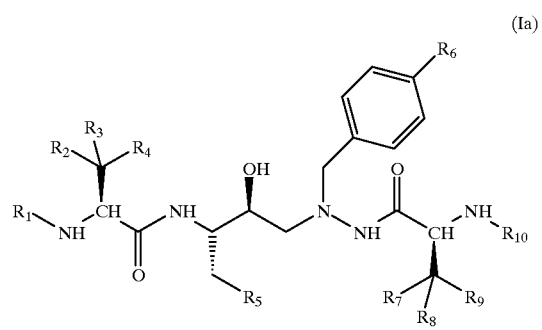

(Ia)

wherein the radicals are as defined.

Salts are especially the pharmaceutically acceptable, non-toxic salts of compounds of formula I.

Such salts are formed, for example, by compounds of formula I with their basic imino group as acid addition salts, preferably with inorganic acids, for example hydrohalic acids, such as hydrochloric acid, sulfuric acid or phosphoric acid, or with strong organic sulfonic, sulfo or phospho acids or N-substituted sulfamic acids (preferably: pKa<1).

For the purposes of isolation or purification it is also possible to use pharmaceutically unacceptable salts, for example perchlorates. Only the pharmaceutically acceptable salts or the free compounds of formula I are used therapeutically and they are therefore preferred.

The compounds of formula I have valuable pharmacological properties. They have anti-retroviral activity, especially against the viruses HIV-1 and HIV-2 which are regarded as causes of AIDS, and surprisingly exhibit synergistic effects in combination with other compounds that are active against retroviral aspartate proteases. The compounds of formula I are inhibitors of retroviral aspartate proteases, especially inhibitors of the aspartate protease of HIV-1 or also HIV-2 and are therefore suitable for the treatment of retroviral diseases, such as AIDS or its preliminary stages (e.g. ARDS). Compounds of formula I also exhibit activity against corresponding animal retroviruses, such as SIV (in apes) or FIV (in cats).

Compounds of formula I exhibit, surprisingly, especially advantageous and important pharmacological properties, for example a very high antiviral activity in cell tests against various virus strains, including those which are resistant to other protease inhibitors, for example in MT2-cells, good pharmacokinetics, such as high bioavailability, high selectivity and, especially, high blood levels (even in the case of oral administration).

The inhibitory action of the compounds of formula I on the proteolytic activity of HIV-1-protease can be shown, for example, analogously to the method described by A. D. Richards et al., J. Biol. Chem. 265(14), 7733–7736 (1990). In that method the inhibition of the action of HIV-1-protease (prepared in accordance with S. Billich et al., J. Biol. Chem. 263(34), 17905–17908 (1990)) is measured in the presence of the icosapeptide RRSNQVSQNYPIVQNIQGRR SEQ ID NO:1, a synthetic substrate of HIV-1-protease, prepared by peptide synthesis in accordance with known procedures, see J. Schneider et al., Cell 54, 363–368 (1988)), which contains as substrate analogue one of the cleavage sites of the gag-precursor protein (natural substrate of HIV-1-protease). That substrate and its cleavage products are analysed by high performance liquid chromatography (HPLC).

The test compound is dissolved in dimethyl sulfoxide. The enzymatic test is carried out by adding suitable dilutions of the inhibitor in 20 mM β-morpholinoethanesulfonic acid (MES) buffer pH 6.0 to the test mixture. That mixture consists of the above-mentioned iscosapeptide (122 $\mu$M) in 20 mM MES-buffer pH 6.0. 100 $\mu$l are used per test batch. The reaction is started by the addition of 10 ml of HIV-1-protease solution and is stopped after one hours incubation at 37° C. by the addition of 10 $\mu$l of 0.3M $HClO_4$. After centrifugation of the sample at 10,000×g for 5 minutes, 20 ml of the resulting supernatant are applied to a 125×4.6 mm Nucleosil® C18-5m-HPLC column (reversed-phase material supplied by Macherey & Nagel, Düren, FRG, based on silica gel that has been charged with $C_{18}$alkyl chains). The uncleaved icosapeptide and its cleavage products are eluted from the column by means of the following gradient: 100% eluant 1→50% eluant 1+50% eluant 2 (eluant 1: 10% acetonitrile, 90% $H_2O$, 0.1% trifluoroacetic acid (TFA); eluant 2: 75% acetonitrile, 25% $H_2O$, 0.08% TFA) for 15 minutes, throughflow rate 1 ml/min. The quantification of the eluted peptide fragments is carried out by measuring the peak height of the cleavage product at 215 nm.

Compounds of formula I exhibit inhibitory actions in the nanomolar range; they preferably exhibit $IC_{50}$ values ($IC_{50}$= that concentration which brings about a 50% reduction in the activity of HIV-1-protease in comparison with a control without inhibitor) of approximately $9 \times 10^{-8}$ to $4 \times 10^{-8}$ M.

An alternative method (see Matayoshi et al., Science 247, 954–958 (1990), here modified) of determining the inhibitory action against HIV-1-protease may be described briefly as follows: the protease (purification: see Leuthardt et al., FEBS Lett. 326, 275–80 (1993)) is incubated at room temperature in 100 $\mu$l of assay buffer (20 mM MES pH 6.0; 200 mM NaCl; 1 mM dithiothreitol; 0.01% polyethylene glycol (average molecular weight 6000 to 8000 da) with 10 $\mu$M fluorogenic substrate SC4400 (4-(4-dimethylaminophenylazo)benzoyl-γ-aminobutyryl-Ser-Gln-Asn-Tyr-Pro-Ile-Val-Gln-EDANS, SEQ ID NO:2, (EDANS=5-(2-aminoethylamino)-1-naphthalenesulfonic acid); Neosystem Laboratoire, France). The reaction is discontinued by the addition of 900 μl of 0.03M $HClO_4$. The HIV-1-protease activity is determined by measuring the increase in fluorescence at λex=336, λem=485 nm. The $IC_{50}$ values of compounds of formula I are determined as the concentration of the compound that is necessary to inhibit the protease activity in the assay by 50%. The numerical values are obtained from computer-generated graphs from data relating to at least 5 concentrations of the compound of formula I in question with threefold determination per concentration.

In a further test it can be shown that compounds of formula I protect cells normally infected by HIV from such an infection or at least slow down such an infection. For this test, MT-2-cells infected with HIV-1/MN are used. MT-2-cells have been transformed with a continuous producer of HTLV-1 (a virus causing leukaemia); they are therefore especially sensitive to the cytopathogenic effect of HIV. MT-2-cells can be obtained via the AIDS Research and Reference Reagent Program, Division of AIDS, NIAID, NIH from Dr. Douglas Richman (see J. Biol. Chem. 263, 5870–5875 (1988) and also Science 229, 563–566 (1985)). The MT-2-cells are cultured in RPMI 1640-medium (Gibco, Scotland; RPMI comprises an amino acid mixture without glutamine) supplemented with 10% heat-inactivated foetal calf serum, glutamine and standard antibiotics. In all cases the cells, and also the virus stock solution used for the infection (HIV-1/MN), are free of mycoplasms. The virus stock solution is prepared as a cell culture supernatant of the permanently infected cell line H9/HIV-1/MN, which can likewise be obtained via the AIDS Research and Reference Program, Division of AIDS, NIAID, NIH from Dr. Robert Gallo (see also Science 224, 500–503 (1984) and Science 226, 1165–1170 (1984)). The titre of the HIV-1/MN virus stock solution (determined by titration onto MT-2-cells) is $4.2 \times 10^5$ TCID50/ml (TCID50=Tissue Culture Infective Dose=dose that infects 50% of the MT-2-cells). In order to measure the infection-inhibiting action of the compounds of formula I, 50 μl of the test compound in question in culture medium and 2800 TCID50 of HIV-1/MN in 100 μl of culture medium are added to $2 \times 10^4$ exponentially growing MT-2-cells which have been applied in 50 μl of culture medium to 96-well microtitre plates (having a round base). After 4 days' incubation (at 37° C., 5% $CO_2$) a 10 μl sample of the supernatant is taken from each well, transferred to a further 96-well microtitre plate and (if necessary) stored at −20° C. In order to measure the activity of the virus-associated reverse transcriptase, 30 μl of reverse transcriptase (RT) cocktail are added to each sample. The reverse transcriptase cocktail consists of 50 mM Tris (α,α,α-tris(hydroxymethyl) methylamine, Ultra pur, Merck, Germany) pH 7.8; 75 mM KCl, 2 mM dithiothreitol, 5 mM $MgCl_2$; 0.1% Nonidet P40 (detergent; Sigma, Switzerland), 0.8 mM EDTA, 10 μg/ml Poly-A (Pharmacia, Uppsala, Sweden) and 0.16 μg/ml oligo (T) (=pdT(12–18), Pharmacia, Uppsala, Sweden) as "template primer"—if desired, the mixture is filtered through a 0.45 mm Acrodisc filter (Gelman Sciences Inc., Ann Arbor, USA). It is stored at −20° C. Prior to the test, 0.1% (v/v) [alpha-$^{32}$P]dTTP is added to aliquots of the solution in order to establish a final radioactivity of 10 μCi/ml.

After mixing, the plate is incubated for 2 hours at 37° C. 5 μl of the reaction mixture are transferred to DE81 paper (Whatman, one filter per well). The dried filters are washed three times for 5 minutes with 300 mM NaCl/25 mM trisodium citrate and then once with ethanol and again dried in the air. The radioactivity on the filters is measured in a Matrix Packard 96-well counter (Packard, Zurich, Switzerland). The $ED_{90}$ values are calculated and are defined as the concentration of the test compound that reduces the RT activity by 90% in comparison with a control without test compound.

Compounds of formula I here exhibit preferably an $ED_{90}$, that is to say a 90% inhibition of virus replication, at concentrations of from $10^{-8}$ to $10^{-9}$M, especially from $5 \times 10^{-9}$ to $10^{-9}$M.

Accordingly, compounds of formula I are suitable for the highly effective retardation of the replication of HIV-1 in cell cultures.

In the determination of the anti-enzymatic activity against numerous human aspartate proteases in accordance with known methods (see, for example, Biochem. J. 265, 871–878 (1990)), compounds of formula I exhibit a high selectivity towards the retroviral aspartate protease of HIV, especially HIV-1. For example, the inhibition constant ($IC_{50}$) for compounds of formula I in the test against cathepsin D is more than 25 μM. The $IC_{50}$ against human cathepsin D in that test is measured at pH 3.1. The test is carried out in accordance with known procedures using the substrate KPIQF*NphRL (see Jupp, R. A., Dunn, B. M., Jacobs, J. W., Vlasuk, G., Arcuri, K. E., Veber, D. F., S. Perow, D. S., Payne, L. S., Boger, J., DeLazio, S., Chakrabarty, P. K, TenBroeke, J., Hangauer, D. G., Ondeyka, D., Greenlee, W. J. and Kay, J.: The selectivity of statine-based inhibitors against various human aspartic proteases. Biochem. J. 265: 871–878 (1990)).

In order to determine their pharmacokinetics, the compounds of formula I are dissolved in dimethyl sulfoxide (DMSO) in a concentration of 240 mg/ml. The resulting solutions are diluted 1:20 (v/v) with 20% (w/v) aqueous hydroxypropyl-β-cyclodextrin solution in order to obtain a concentration of the test compound in question of 12 mg/ml. The resulting solution is treated briefly with ultrasound and administered orally to female BALB/c mice (Bomholtgarden, Copenhagen, Denmark) by artificial tube feeding at a dose of 120 mg/kg. At fixed times (for example 30, 60, 90, 120 min) after administration, mice are sacrificed and the plasma stored in heparinised test tubes. The blood is centrifuged (12,000×g, 5 min) and the plasma removed. The plasma is deproteinised by the addition of an equal volume of acetonitrile. The mixture is mixed using a vortex mixer and and left to stand at room temperature for 20 to 30 minutes. The precipitate is pelleted by centrifugation (12,000×g, 5 min), and the concentration of the test compound is determined by reversed phase high performance liquid chromatography (HPLC).

The HPLC analysis of the samples obtained in accordance with the method described above is carried out on a 125×4.6 mm Nucleosil® $C_{18}$-column (reversed-phase material supplied by Macherey & Nagel, Düren, Germany, based on silica gel derivatised with carbon radicals having 18 carbon atoms), using a 2 cm long preliminary column of the same column material. The test is carried out with the following linear acetonitrile/water gradient (in each case in the presence of 0.05% trifluoroacetic acid): 20% acetonitrile to 100% acetonitrile for 20 min; then 5 min 100% acetonitrile; then returning to the initial conditions for 1 min and 4 min reequilibration. The flow rate is 1 ml/min. Under those conditions the compound of formula I from Example 1, for example, has a retention time of about 15.5 minutes, and its detection limit is 0.1–0.2 μM. The test compound is detected by UV absorption measurement at 255 nm. Peaks are identified by the retention time and the UV spectrum between 205 and 400 nm. The concentrations are determined by the external standard method; the peak heights are obtained for determining the concentrations by comparison with standard curves. The standard curves are obtained by analogous HPLC analysis of mouse plasma that contains known concentrations of the test compound in question and that has been worked up in accordance with the method described above.

In that experiment compounds of formula I produce plasma concentrations far above the $ED_{90}$ determined above in the cell experiment, for example from 0.5 to 7 $\mu$M, especially from 1 to 7 $\mu$M, after 30 minutes and from 1 to 6 $\mu$M after 90 minutes; for example, the compound of formula I from Example 1 exhibits a plasma level of 6.33 $\mu$M 30 minutes after oral administration, and 5.35 $\mu$M after 90 minutes.

In particular, the combination of high bioavailability (high plasma levels), which is surprising on its own, and the unexpectedly excellent $ED_{90}$ in the cell experiment makes the compounds of the present invention valuable in an unforeseen way.

In the determination of the anti-enzymatic activity against numerous human aspartate proteases in accordance with known methods (see, for example, Biochem. J. 265, 871–878 (1990)), compounds of formula I exhibit a high selectivity towards the retroviral aspartate protease of HIV, especially HIV-1.

The compounds of formula I can be used alone or in combination (as a set combination of corresponding compositions or as a combination of individual compounds or individual compositions in a time-staggered sequence) with other substances (or salts thereof provided that at least one salt-forming group is present) that are effective against retroviruses, especially HIV, such as HIV-1 or HIV-2; especially with inhibitors of reverse transcriptase, more especially nucleoside analogues, especially 3'-azido-3'-deoxypyrimidine (=zidovudine=®RETROVIR, Burroughs-Wellcome), 2',3'-dideoxycytidine (=zalcitabine=®HIVID, Hoffmann-LaRoche), 2',3'-dideoxyinosine (=didanosine=®VIDEX, Bristol-Myers-Squibb) or (2R,cis)-4-amino-1-(2-hydroxymethyl-1,3-oxathiolan-5-yl)-(1H)-pyrimidin-2-one (=lamivudine, Glaxo) or non-nucleoside analogues, such as 11-cyclopropyl-5,11-dihydro-4-methyl-(6H)-dipyrido[3,2-b;2',3'-e]-[1,4]diazepin-6-one; or with one or more (especially one or also two) other inhibitors of retroviral aspartate proteases, especially aspartate proteases of HIV, such as HIV-1 and HIV-2, especially a) one of the inhibitors mentioned in EP 0 346 847 (published on Dec. 20, 1989) and EP 0 432 695 (published on Jun. 19, 1991; corresponds to U.S. Pat. No. 5,196,438, published on Mar. 23, 1993), especially the compound designated Ro 31-8959 (=saquinavir; Hoffmann-LaRoche);

b) one of the inhibitors mentioned in EP 0 541 168 (published on May 12, 1993; corresponds to U.S. Pat. No. 5,413,999), especially the compound designated L-735,524 (=indinavir=®CRIXIVAN; Merck & Co., Inc.);

c) one of the inibitors mentioned in EP 0 486 948 (published on May 27, 1992; corresponds to U.S. Pat. No. 5,354,866), especially the compound designated ABT-538 (=ritonavir; Abbott);

d) the compound designated KVX-478 (or VX-478 or 141W94; GlaxoWellcome, Vertex and Kissei Pharmaceuticals)

e) the compound designated AG-1343 (Agouron);

f) the compound designated KNI-272 (Nippon Mining);

g) the compound designated U-96988 (Upjohn); and/or h) the compound designated BILA-2011 BS (=palinavir; Boehringer-Ingelheim), or in each case a salt thereof provided that salt-forming groups are present.

The compounds of formula I can also be used in the prevention, control and treatment of retrovirus infections, especially HIV, such as HIV-1 or HIV-2, in cell cultures, especially cell cultures of lymphocyte cell lines, from warm-blooded animals, which is advantageous especially in the case of very valuable cell cultures that produce, for example, specific antibodies, vaccines or messenger substances, such as interleukins and the like, and are therefore of great commercial value.

Finally, the compounds of formula I can be used as standards in experiments, for example as HPLC standards or as standards for the comparison of animal models in respect of different aspartate protease inhibitors, for example in respect of the blood levels achievable.

In the groups of preferred compounds of formula I mentioned below, it is possible where expedient (for example in order to replace more general definitions by more specific definitions or, especially, by definitions described as being preferred) to use definitions of substituents from the general definitions given above; in each case preference is given to the definitions described above as being preferred or given as examples.

Preference is given to compounds of formula I, especially of formula Ia, wherein $R_1$ and $R_{10}$ are each independently of the other lower alkoxycarbonyl;

either $R_2$, $R_3$ and $R_4$ are each independently of the other $C_1$–$C_4$alkyl and $R_7$, $R_8$ and $R_9$ are each selected from hydrogen and $C_1$–$C_4$alkyl, but not more than one of the radicals may be hydrogen;

or (preferably) $R_7$, $R_8$ and $R_9$ are each independently of the other $C_1$–$C_4$alkyl and $R_2$, $R_3$ and $R_4$ are each selected from hydrogen and $C_1$–$C_4$alkyl, but not more than one of the radicals may be hydrogen;

$R_5$ is phenyl or cyclohexyl; and $R_6$ is phenyl or cyanophenyl;

or salts thereof.

Greater preference is given to compounds of formula I, especially of formula Ia, wherein $R_1$ and $R_{10}$ are each independently of the other tert-butoxy- or especially ethoxy- or more especially methoxy-carbonyl;

either $R_2$, $R_3$ and $R_4$ are each independently of the other methyl and $R_7$, $R_8$ and $R_9$ are each selected from hydrogen and methyl, but not more than one of the radicals may be hydrogen;

or (preferably) $R_7$, $R_8$ and $R_9$ are each independently of the other methyl and $R_2$, $R_3$ and $R_4$ are each selected from hydrogen and methyl, but not more than one of the radicals may be hydrogen;

$R_5$ is phenyl; and $R_6$ is phenyl or 2-cyanophenyl;

or salts thereof.

Greatest preference is given to the compounds of formula I mentioned in the Examples, or pharmaceutically acceptable salts thereof provided that at least one salt-forming group is present.

The compound of formula I having the name 1-(4-biphenylyl)-2-N-(N-methoxycarbonyl-(L)-tert-leucyl)-amino-4(S)-hydroxy-5(S)-N-(N-methoxycarbonyl-(L)-valyl)-amino-6-phenyl-2-azahexane (formula: 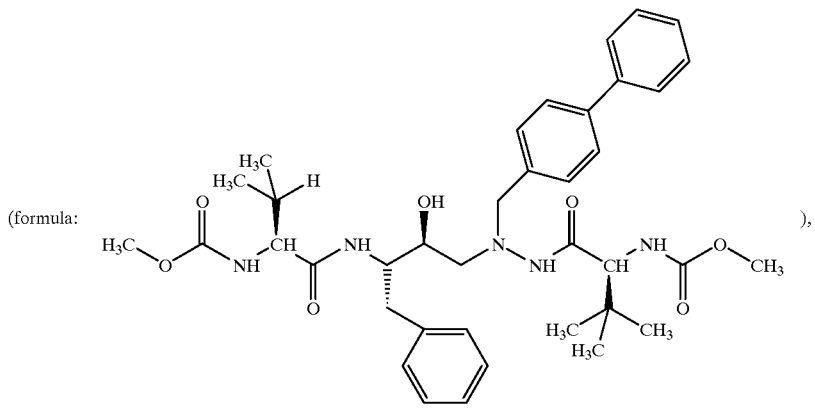 ), or a pharmaceutically acceptable salt thereof, is especially preferred.

Special preference is given also to the compound of formula I having the name 1-(4(2-cyanophenyl)phenyl)-2-N-(N-methoxycarbonyl-(L)-tert-leucyl)-amino-4(S)-hydroxy-5(S)-N-(N-methoxycarbonyl-(L)-valyl)-amino-6-phenyl-2-azahexane, or a pharmaceutically acceptable salt thereof.

Very special preference is given also to the compound of formula I having the name 1-(4-biphenyl)-4(S)-hydroxy-5(S)-2,5-bis[N-(N-methoxycarbonyl-(L)-tert-leucyl)-amino]-6-phenyl-2-azahexane, or a pharmaceutically acceptable salt thereof.

The compounds of formula I and salts of those compounds having at least one salt-forming group are prepared according to processes known per se, for example as follows:

a) a hydrazine derivative of formula

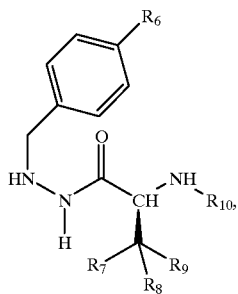

(III)

wherein the radicals $R_6$, $R_7$, $R_8$, $R_9$ and $R_{10}$ are as defined for compounds of formula I, is added to an epoxide of formula

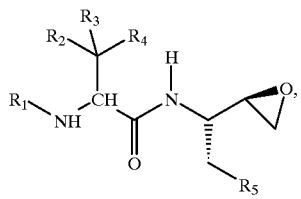

(IV)

wherein the radicals $R_1$, $R_2$, $R_3$, $R_4$ and $R_5$ are as defined for compounds of formula I, free functional groups with the exception of those participating in the reaction being, if necessary, in protected form, and any protecting groups are removed, or b) an amino compound of formula

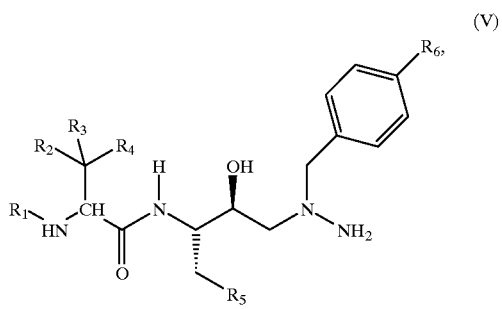

(V)

wherein the radicals $R_1$, $R_2$, $R_3$, $R_4$, $R_5$ and $R_6$ are as defined for compounds of formula I, is condensed with an acid of formula

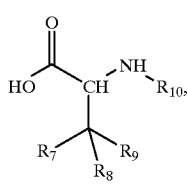

(VI)

or with a reactive acid derivative thereof, wherein the radicals $R_7$, $R_8$, $R_9$ and $R_{10}$ are as defined for compounds of formula I, free functional groups with the exception of those participating in the reaction being, if necessary, in protected form, and any protecting groups are removed, or c) an amino compound of formula

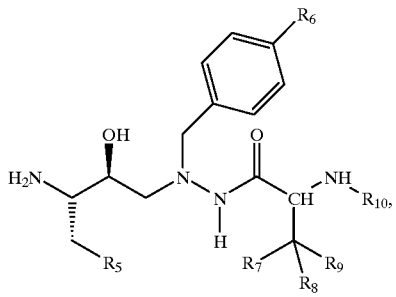
(VII)

wherein the radicals $R_5$, $R_6$, $R_7$, $R_8$, $R_9$ and $R_{10}$ are as defined for compounds of formula I, is condensed with an acid of formula

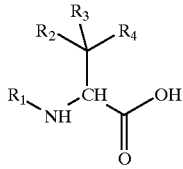
(VIII)

or with a reactive acid derivative thereof, wherein $R_1$, $R_2$, $R_3$ and $R_4$ are as defined for compounds of formula I, free functional groups with the exception of those participating in the reaction being, if necessary, in protected form, and any protecting groups are removed, or d) for the preparation of compounds of formula I wherein the substituent pairs $R_9$ and $R_{10}$, $R_2$ and $R_7$, $R_3$ and $R_8$ and $R_4$ and $R_9$ each represent two identical radicals, as defined for compounds of formula I, but none of the radicals $R_2$, $R_3$, $R_4$, $R_7$, $R_8$ and $R_9$ is hydrogen, and $R_5$ and $R_6$ are as defined for compounds of formula I, a diamino compound of formula

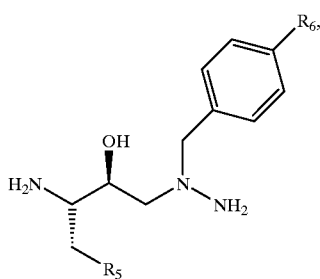
(IX)

wherein the radicals are as defined immediately above, is condensed with an acid of formula

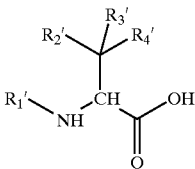
(VIIIa)

or with a reactive acid derivative thereof, wherein $R_1'$, $R_2'$, $R_3'$ and $R_4'$ are as defined for $R_1$ and $R_{10}$, $R_2$ and $R_7$, $R_3$ and $R_8$, and $R_4$ and $R_9$ in formula I, the pairs $R_1$ and $R_{10}$, $R_2$ and $R_7$, $R_3$ and $R_8$ and $R_4$ and $R_9$ each representing two identical radicals and none of the radicals $R_2$, $R_3$, $R_4$, $R_7$, $R_8$ and $R_9$ being hydrogen, and free functional groups with the exception of those participating in the reaction being, if necessary, in protected form, and any protecting groups are removed, or e) an imino compound of formula I'

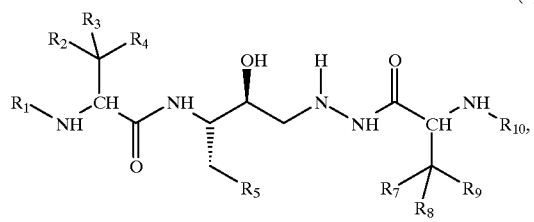
(I')

wherein the radicals $R_1$, $R_2$, $R_3$, $R_4$, $R_5$, $R_7$, $R_8$, $R_9$ and $R_{10}$ are as defined for compounds of formula I, is reacted with a compound of formula X

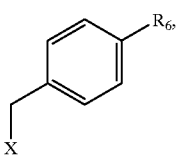
(X)

wherein X is a leaving group and $R_6$ is as defined for compounds of formula I, free functional groups with the exception of those participating in the reaction being, if necessary, in protected form, and any protecting groups are removed, or f) an imino compound of formula I'

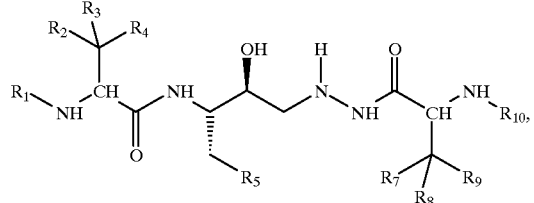
(I')

wherein the radicals $R_1$, $R_2$, $R_3$, $R_4$, $R_5$, $R_7$, $R_8$, $R_9$ and $R_{10}$ are as defined for compounds of formula I, is reacted, with reductive alkylation, with an aldehyde of formula X*

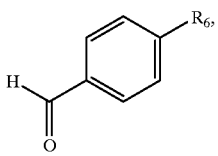

(X*)

wherein $R_6$ is as defined for compounds of formula I, or a reactive derivative thereof, free functional groups with the exception of those participating in the reaction being, if necessary, in protected form, and any protecting groups are removed, and, if desired, a compound of formula I having at least one salt-forming group obtainable in accordance with any one of processes a) to f) above is converted into a salt or an obtainable salt is converted into the free compound or into a different salt and/or isomeric mixtures which may be obtainable are separated and/or a compound of formula I according to the invention is converted into a different compound of formula I according to the invention.

The above processes are described in more detail below with reference to preferred embodiments.

In the following description of the individual processes and the preparation of the starting materials, unless otherwise indicated the radicals $R_1$, $R_2$, $R_3$, $R_4$, $R_5$, $R_6$, $R_7$, $R_8$, $R_9$ and $R_{10}$ are as defined for compounds of formula I.

Process a) (Addition of an amine to an epoxide):

In the hydrazine derivatives of formula III, the amino group participating in the reaction preferably has a free hydrogen atom; it may, however, itself have been derivatised in order to increase the reactivity of the hydrazine derivative.

The epoxide of formula IV enables the terminal addition of the hydrazine derivative to proceed in the preferred manner.

In starting materials, functional groups the reaction of which is to be avoided, especially carboxy, amino and hydroxy groups, can be protected by suitable protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis and the like. In certain cases the protecting groups can additionally cause reactions to proceed selectively, for example stereoselectively. It is characteristic of protecting groups that they can be removed easily, i.e. without undesired secondary reactions taking place, for example by solvolysis, reduction, photolysis, and also enzymatically, for example also under physiological conditions. Radicals analogous to protecting groups may also be present in the end products, however. Compounds of formula I having protected functional groups may have greater metabolic stability or pharmacodynamic properties that are better in some other way than the corresponding compounds having free functional groups. Hereinabove and hereinbelow, protecting groups are referred to in their true sense when the radicals in question are not present in the end products.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie" ("Methods of Organic Chemistry"), Houben-Weyl, 4th edition, Volume 15/I, Georg Thieme Verlag, Stuttgart 1974, in H.-D. Jakubke and H. Jescheit, "Aminosäuren, Peptide, Proteine" ("Amino acids, peptides, proteins"), Verlag Chemie, Weinheim, Deerfield Beach and Basle 1982, and in Jochen Lehmann, "Chemie der Kohlenhydrate: Monosaccharide und Derivate" ("The Chemistry of Carbohydrates: monosaccharides and derivatives"), Georg Thieme Verlag, Stuttgart 1974.

A carboxy group is protected, for example, in the form of an ester group which can be cleaved selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or tri-substituted, for example, by lower alkyl, for example tert-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)methoxycarbonyl, and also carboxy esterified by a lower alkyl group, the lower alkyl group being substituted in the 1- or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, as well as 2-(tri-substituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-tri-lower alkylsilylethoxycarbonyl, for example 2-trimethylsilylethoxycarbonyl or 2-(di-n-butyl-methyl-silyl)ethoxycarbonyl, or 2-triarylsilylethoxycarbonyl, such as triphenylsilylethoxycarbonyl.

A carboxy group may also be protected in the form of an organic silyloxycarbonyl group. An organic silyloxycarbonyl group is, for example, a tri-lower alkylsilyloxycarbonyl group, for example trimethylsilyloxycarbonyl.

A protected carboxy group is preferably tert-lower alkoxycarbonyl, for example tert-butoxycarbonyl, benzyloxycarbonyl, 4-nitrobenzyloxycarbonyl, 9-fluorenylmethoxycarbonyl or diphenylmethoxycarbonyl.

A protected amino group may be protected by an amino-protecting group, for example in the form of an acylamino, arylmethylamino, etherified mercaptoamino, 2-acyl-lower alk-1-enylamino or silylamino group or in the form of an azido group.

In a corresponding acylamino group, acyl is, for example, the acyl radical of an organic carboxylic acid having, for example, up to 18 carbon atoms, especially an unsubstituted or substituted, for example halo- or aryl-substituted, lower alkanecarboxylic acid or an unsubstituted or substituted, for example halo-, lower alkoxy- or nitro-substituted, benzoic acid, or, preferably, of a carbonic acid semiester. Such acyl groups are, for example, lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, unsubstituted or substituted, for example halo-, lower alkoxy or nitro-substituted, benzoyl, such as benzoyl, 4-chlorobenzoyl, 4-methoxybenzoyl or 4-nitrobenzoyl, lower alkoxycarbonyl, preferably lower alkoxycarbonyl that is branched in the 1-position of the lower alkyl radical or suitably substituted in the 1- or 2-position, for example tert-lower alkoxycarbonyl, such as tert-butoxycarbonyl, arylmethoxycarbonyl having one, two or three aryl radicals which are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(tri-substituted silyl)-lower alkoxycarbonyl, for example 2-tri-lower alkylsilyl-lower alkoxycarbonyl, such as 2-trimethylsilylethoxycarbonyl or 2-(di-n-butylmethylsilyl)-ethoxycarbonyl, or triarylsilyl-lower alkoxycarbonyl, for example 2-triphenylsilylethoxycarbonyl.

In an arylmethylamino group, for example a mono-, di- or especially tri-arylmethylamino group, the aryl radicals are especially unsubstituted or substituted phenyl radicals. Such groups are, for example, benzyl-, diphenylmethyl- or especially trityl-amino.

In an etherified mercaptoamino group the mercapto group is especially in the form of substituted arylthio or aryl-lower alkylthio wherein aryl is, for example, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk-1-en-2-yl, for example lower alkoxycarbonyl-prop-1-en-2-yl, such as 1-ethoxycarbonyl-prop-1-en-2-yl.

A silylamino group is, for example, a tri-lower alkylsilylamino group, for example trimethylsilylamino or tert-butyl-dimethylsilylamino. The silicon atom of the silylamino group can also be substituted by only two lower alkyl groups, for example methyl groups, and by the amino group or carboxy group of a second molecule of formula I. Compounds having such protecting groups can be prepared, for example, using the corresponding chlorosilanes, such as dimethylchlorosilane, as silylating agents.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl.

A hydroxy group can be protected, for example, by an acyl group, for example lower alkanoyl that is substituted by halogen, such as chlorine, such as 2,2-dichloroacetyl, or especially by an acyl radical of a carbonic acid semiester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A hydroxy group can also be protected by tri-lower alkylsilyl, for example trimethylsilyl, triisopropylsilyl or tert-butyl-dimethylsilyl, a readily removable etherifying group, for example an alkyl group, such as tert-lower alkyl, for example tert-butyl, an oxa- or a thia-aliphatic or cycloaliphatic, especially 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thiacycloalkyl having from 5 to 7 ring atoms, such as 2-tetrahydrofuryl or 2-tetrahydropyranyl, or a corresponding thia analogue, and also by 1-phenyl-lower alkyl, such as benzyl, diphenylmethyl or trityl, wherein the phenyl radicals can be substituted, for example, by halogen, for example chlorine, lower alkoxy, for example methoxy, and/or by nitro.

A hydroxy group and an amino group that are adjacent to one another in a molecule can be protected, for example, by bivalent protecting groups, such as a methylene group that is preferably substituted, for example by one or two lower alkyl radicals or by oxo, for example unsubstituted or substituted alkylidene, for example lower alkylidene, such as isopropylidene, cycloalkylidene, such as cyclohexylidene, a carbonyl group or benzylidene.

In the context of this disclosure, a protecting group, for example a carboxy-protecting group, is to be understood as being expressly also a polymeric carrier that is bonded in a readily removable manner to the functional group, for example the carboxy group, to be protected, for example a carrier suitable for the Merrifield synthesis. Such a suitable polymeric carrier is, for example, a polystyrene resin weakly cross-linked by copolymerisation with divinylbenzene and carrying bridge members suitable for reversible bonding.

The addition of the compounds of formula III to the epoxides of formula IV is carried out preferably under the reaction conditions customarily used for the addition of nucleophiles to epoxides.

The addition is carried out especially in aqueous solution and/or in the presence of polar solvents, such as alcohols, for example methanol, ethanol, isopropanol or ethylene glycol, ethers, such as dioxane, amides, such as dimethylformamide, or phenols, such as phenol, and also under anhydrous conditions, in nonpolar solvents, such as benzene or toluene, or in benzene/water emulsions, optionally in the presence of acidic or basic catalysts, for example alkali hydroxide solutions, such as sodium hydroxide solution, or in the presence of solid phase catalysts doped with the hydrazine, such as aluminium oxide, in ethers, for example diethyl ether, generally at temperatures of from approximately 0° C. to the boiling temperature of the reaction mixture in question, preferably from 20° C. to reflux temperature, optionally under elevated pressure, for example in a bomb tube, in which case it is also possible to exceed the boiling temperature, and/or under an inert gas, such as nitrogen or argon, it being possible for each of the two compounds of formulae III and IV to be present in excess, for example in a molar ratio of from 1:1 to 1:100, preferably in a molar ratio of from 1:1 to 1:10, more especially in a ratio of from 1:1 to 1:3.

The freeing of protected groups may be effected in accordance with the methods described under the heading "Removal of protecting groups".

Process b) (Formation of an amide bond)

In starting materials of formulae V and VI, functional groups, with the exception of groups that are to participate in the reaction or that do not react under the reaction conditions, are protected independently of one another by one of the protecting groups mentioned under Process a).

The compounds of formula VI either contain a free carboxy group or are in the form of a reactive acid derivative thereof, for example in the form of a derived activated ester or reactive anhydride, or in the form of a reactive cyclic amide. The reactive acid derivatives may also be formed in situ.

Activated esters of compounds of formula VI having a terminal carboxy group are especially esters unsaturated at the carbon atom linking the radical to be esterified, for example esters of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-di-substituted carbodiimide, for example N,N'-dicyclohexylcarbodiimide or especially N-(3-dimethylaminopropyl)-N'-ethylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thio esters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene 2,3-dicarboxylic acid imide, 1-hydroxybenzotriazole or 3-hydroxy-3,4-dihydro-1,2,3-benzo triazin-4-one, for example by the anhydride or carbodiimide method; activated N-hydroxy esters method). Internal esters, for example γ-lactones, can also be used.

Anhydrides of acids may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride, phosgene or oxalyl chloride; acid chloride method), azides (obtainable, for example, from a corresponding acid ester via the corresponding hydrazide and treatment thereof with nitrous acid; azide method), anhydrides with carbonic acid semiesters, for example carbonic acid lower alkyl semiesters (especially chloroformic acid methyl esters) (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate or by reaction of alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides with five-membered diazacycles of aromatic character, such as amides with imidazoles, for example imidazole (obtainable, for example, by treatment of the corresponding acid with N,N'-carbonyldiimidazole; imidazole method), or pyrazole, for example 3,5-dimethylpyrazole (obtainable, for example, via the acid hydrazide by treatment with acetylacetone; pyrazolide method).

As mentioned, derivatives of carboxylic acids used as acylating agents may also be formed in situ. For example, N,N'-disubstituted amidino esters may be formed in situ by reacting a mixture of the starting material of formula V and the acid used as acylating agent in the presence of a suitable N,N'-disubstituted carbodiimide, for example N,N'-cyclohexylcarbodiimide or especially N-(3-dimethylaminopropyl)-N'-ethylcarbodiimide. In addition, amino or amido esters of the acids used as acylating agents may be formed in the presence of the starting material of formula V to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, where appropriate in the presence of a suitable base, for example 4-dimethylamino-pyridine. Furthermore, activation in situ can be achieved by reaction with N,N,N',N'-tetraalkyluronium compounds, such as O-benzotriazol-1-yl-N,N,N',N'-tetramethyluronium hexafluorophosphate, O-(1, 2-dihydro-2-oxo-1-pyridyl)-N,N,N',N'-tetramethyluronium tetrafluoroborate or O-(3,4-dihydro-4-oxo-1,2,3-benzotriazolin-3-yl)-N,N,N',N'-tetramethyluronium tetrafluoroborate. Finally, phosphoric acid anhydrides of the carboxylic acids of formula VI can be prepared in situ by reacting an alkylphosphoric acid amide, such as hexamethylphosphoric acid triamide, in the presence of a sulfonic acid anhydride, such as 4-toluenesulfonic acid anhydride, with a salt, such as a tetrafluoroborate, for example sodium tetrafluoroborate, or with another derivative of hexamethylphosphoric acid triamide, such as benzotriazol-1-yl-oxy-tris(dimethylamino)phosphonium hexafluoride, preferably in the presence of a racemisation-reducing additive, such as N-hydroxybenzotriazole.

The amino group of compounds of formula V that participates in the reaction preferably carries at least one reactive hydrogen atom, especially when the carboxy, sulfonyl or phosphoryl group reacting therewith is present in reactive form; it may, however, itself have been derivatised, for example by reaction with a phosphite, such as diethylchlorophosphite, 1,2-phenylene chlorophosphite, ethyldichlorophosphite, ethylene chlorophosphite or tetraethylpyrophosphite. A derivative of such a compound having an amino group is, for example, also a carbamic acid halide or an isocyanate, the amino group that participates in the reaction being substituted by halocarbonyl, for example chlorocarbonyl, or modified in the form of an isocyanate group, respectively.

Condensation to form an amide bond can be carried out in a manner known per se, for example as described in standard works, such as Houben-Weyl, "Methoden der organischen Chemie", 4th edition, Volume 15/II (1974), Volume IX (1955), Volume E11 (1985), Georg Thieme Verlag, Stuttgart, "The Peptides" (E. Gross and J. Meienhofer, eds.), Volumes 1 and 2, Academic Press, London and New York, 1979/1980, or M. Bodansky, "Principles of Peptide Synthesis", Springer-Verlag, Berlin 1984.

The condensation of a free carboxylic acid with the appropriate amine can be carried out preferably in the presence of one of the customary condensation agents, or using carboxylic acid anhydrides or carboxylic acid halides, such as chlorides, or activated carboxylic acid esters, such as p-nitrophenyl esters. Customary condensation agents are, for example, carbodiimides, for example diethyl-, dipropyl-, or dicyclohexyl-carbodiimide or especially N-(3-dimethylaminopropyl)-N'-ethylcarbodiimide, also suitable carbonyl compounds, for example carbonylimidazole, 1,2-oxazolium compounds, for example 2-ethyl-5-phenyl-1,2-oxazolium-3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate or especially O-(1,2-dihydro-2-oxo-1-pyridyl)-N,N,N',N'-tetramethyluronium tetrafluoroborate, also activated phosphoric acid derivatives, for example diphenylphosphorylazide, diethylphosphorylcyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate.

If desired, an organic base may be added, preferably a tertiary amine, for example a tri-lower alkylamine, especially ethyldiisopropylamine or more especially triethylamine, and/or a heterocyclic base, for example 4-dimethylaminopyridine or preferably N-methylmorpholine or pyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (if desired together with a sulfate).

Carboxylic acid chlorides, for example the chlorocarbonic acid derivatives derived from the acid of formula VI, are condensed with the corresponding amines preferably in the presence of an organic amine, for example the above-mentioned tri-lower alkylamines or heterocyclic bases, where appropriate in the presence of a hydrogen sulfate or a hydroxide, preferably an alkali metal hydroxide, such as sodium hydroxide.

The condensation is preferably carried out in an inert, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran or dioxane, an ester, for example ethyl acetate, or a nitrile, for example acetonitrile, or in a mixture thereof, as appropriate at reduced or elevated temperature, for example in a temperature range of from approximately −40° to approximately +100° C, preferably from approximately −10° to approximately +70° C., and when arylsulfonyl esters are used also at approximately from +100° to +200° C., and if necessary under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone may also be added where appropriate.

The condensation can also be carried out in accordance with the technique known as solid-phase synthesis which originates from R. Merrifield and is described, for example, in Angew. Chem. 97, 801–812 (1985), Naturwissenschaften 71, 252–258 (1984) or in R. A Houghten, Proc. Natl. Acad. Sci. USA 82, 5131–5135 (1985).

The freeing of protected groups may be effected in accordance with the methods described under the heading "Removal of protecting groups."

Process c) (Formation of an amide bond)

In starting materials of formulae VII and VIII, functional groups, with the exception of groups that are to participate in the reaction or that do not react under the reaction conditions, are protected independently of one another by one of the protecting groups mentioned under Process a).

The process is entirely analogous to that given under Process b) but compounds of formula VII are used instead of those of formula V and compounds of formula VIII are used instead of those of formula VI.

The freeing of protected groups may be effected in accordance with the methods described under the heading "Removal of protecting groups".

Process d) (Formation of an amide bond)

In starting materials of formula IX and in the acid of formula VIIIa suitable for the introduction of the identical acyl radicals, or in reactive derivatives thereof, functional groups, with the exception of groups that are to participate in the reaction or that do not react under the reaction conditions, are protected independently of one another by one of the protecting groups mentioned under Process a).

Preferred starting compounds of formula IX, which may be protected by protecting groups, are those described below in the section relating to starting compounds.

The process is entirely analogous to that given under Process b) but compounds of formula IX are used instead of those of formula V and compounds of formula VIIIa are used instead of those of formula VI.

The freeing of protected groups may be effected in accordance with the methods described under the heading "Removal of protecting groups".

Process e) (Alkylation of a secondary nitrogen atom)

In starting materials of formula I' and formula X or in reactive derivatives thereof, functional groups, with the exception of groups that are to participate in the reaction or that do not react under the reaction conditions, are protected independently of one another by one of the protecting groups mentioned under Process a).

A leaving group X is especially a nucleofugal leaving group selected from hydroxy esterified by a strong inorganic or organic acid, such as hydroxy esterified by a mineral acid, for example a hydrohalic acid, such as hydrochloric, hydrobromic or hydriodic acid, hydroxy esterified by a strong organic sulfonic acid, such as a lower alkanesulfonic acid that is unsubstituted or substituted, for example, by halogen, such as fluorine, or by an aromatic sulfonic acid, for example benzenesulfonic acid that is unsubstituted or substituted by lower alkyl, such as methyl, halogen, such as bromine, and/or by nitro, for example a methanesulfonic, p-bromotoluenesulfonic or p-toluenesulfonic acid, and hydroxy esterified by hydrazoic acid.

The substitution can take place under the conditions of a first or second order nucleophilic substitution.

For example, one of the compounds of formula X wherein X is a leaving group having high polarisability of the electron shell, for example iodine, can be used in a polar aprotic solvent, for example acetone, acetonitrile, nitromethane, dimethyl sulfoxide or dimethylformamide. The reaction can also be carried out in water, optionally in admixture with an organic solvent, for example ethanol, tetrahydrofuran or acetone, as solubiliser. The substitution reaction is carried out, as appropriate, at reduced or elevated temperature, for example in a temperature range of from approximately −40° to approximately 100° C., preferably from approximately −10° to approximately 50° C., and optionally under an inert gas, for example under a nitrogen or argon atmosphere.

The freeing of protected groups may be effected in accordance with the methods described under the heading "Removal of protecting groups".

Process f) (Reductive alkylation of a secondary amino group)

In starting materials of formula I' and formula X* or in reactive derivatives thereof, functional groups, with the exception of groups that are to participate in the reaction or that do not react under the reaction conditions, are protected independently of one another by one of the protecting groups mentioned under Process a).

Reactive derivatives of the compounds of formula I are, for example, corresponding bisulfite adducts or especially semiacetals or ketals of compounds of formula X* with alcohols, for example lower alkanols; or thioacetals of compounds of formula X* with mercaptans, for example lower alkanesulfides. The free aldehydes of formula X* are preferred.

The reductive alkylation is preferably carried out with hydrogenation in the presence of a catalyst, especially a noble metal catalyst, such as platinum or especially palladium, which is preferably bonded to a carrier material, such as carbon, or a heavy metal catalyst, such as Raney nickel, at normal pressure or at pressures of from 0.1 to 10 MegaPascal (MPa), or with reduction by means of complex hydrides, such as borohydrides, especially alkali metal cyanoborohydrides, for example sodium cyanoborohydride, in the presence of a suitable acid, preferably relatively weak acids, such as lower alkanecarboxylic acids or especially a sulfonic acid, such as p-toluenesulfonic acid; in customary solvents, for example alcohols, such as methanol or ethanol, in the presence or absence of water.

The freeing of protected groups may be effected in accordance with the methods described under the heading "Removal of protecting groups".

Removal of protecting groups

The removal of protecting groups that are not constituents of the desired end product of formula I, for example carboxy-, amino- and hydroxy-protecting groups, is effected in a manner known per se, for example by means of solvolysis, especially hydrolysis, alcoholysis or acidolysis, or by means of reduction, especially hydrogenolysis or chemical reduction, and also photolysis, stepwise or simultaneously as appropriate, it being possible also to use enzymatic methods. The removal of the protecting groups is described, for example, in the standard works mentioned hereinabove in the section relating to protecting groups.

For example, protected carboxy, for example tert-lower alkoxycarbonyl, lower alkoxycarbonyl substituted in the 2-position by a trisubstituted silyl group or in the 1-position by lower alkoxy or by lower alkylthio, or unsubstituted or substituted diphenylmethoxycarbonyl can be converted into free carboxy by treatment with a suitable acid, such as formic acid, hydrogen chloride or trifluoroacetic acid, where appropriate with the addition of a nucleophilic compound, such as phenol or anisole. Carboxy can be freed from lower alkoxycarbonyl also by bases, such as hydroxides, for example alkali metal hydroxides, such as NaOH or KOH. Unsubstituted or substituted benzyloxycarbonyl can be cleaved, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. 2-(Tri-substituted silyl)-lower alkoxycarbonyl, such as 2-tri-lower alkylsilyl-lower alkoxycarbonyl, can also be converted into free carboxy by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example using trypsin.

A protected amino group is freed in a manner known per se and, according to the nature of the protecting groups, in various ways, preferably by solvolysis or reduction. Lower alkoxycarbonylamino, such as tert-butoxycarbonylamino, can be cleaved in the presence of acids, for example mineral acids, for example a hydrogen halide, such as hydrogen chloride or hydrogen bromide, or sulfuric or phosphoric acid, but preferably hydrogen chloride, or in the presence of strong organic acids, such as a trihaloacetic acid, for example trifluoroacetic acid, or formic acid, in polar solvents, such as water, or ethers, preferably cyclic ethers, such as dioxane; 2-halo-lower alkoxycarbonylamino (where appropriate after conversion of a 2-bromo-lower alkoxycarbonylamino group into a 2-iodo-lower alkoxycarbonylamino group), or, dissolved directly in a liquid organic carboxylic acid, such as formic acid, aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-(tri-substituted silyl)-lower alkoxycarbonylamino, such as 2-tri-lower alkylsilyl-lower alkoxycarbonylamino, can be cleaved by treatment with a suitable acid, for example formic acid or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a platinum or palladium catalyst, unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water, and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting substitution product, and amino is freed from trifluoroacetylamino, for example, by hydrogenolysis with bases, such as alkali metal hydroxides or carbonates, such as $Na_2CO_3$ or $K_2CO_3$, in polar solvents, for example alcohols, such as methanol, in the presence or absence of water, at temperatures of from 0° to 100° C., especially at reflux temperature. An amino group protected by 2-(tri-substituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group. Likewise, silyl, such as trimethylsilyl, bonded directly to a hetero atom, such as nitrogen, can be removed using fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or in a mixture of water and an organic solvent, such as an alcohol or dioxane, at approximately from 20° C. to 25° C., or with cooling or heating.

A hydroxy group protected by a suitable acyl group, by a tri-lower alkylsilyl group or by unsubstituted or substituted 1-phenyl-lower alkyl is freed analogously to a correspondingly protected amino group. A hydroxy group protected by 2,2-dichloroacetyl is freed, for example, by basic hydrolysis, and a hydroxy group protected by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Adjacent hydroxy and amino groups that are protected together by a bivalent protecting group, preferably, for example, by a methylene group mono- or di-substituted by lower alkyl, such as by lower alkylidene, for example isopropylidene, cycloalkylidene, for example cyclohexylidene, or benzylidene, can be freed by acid solvolysis, especially in the presence of a mineral acid or a strong organic acid. A tri-lower alkylsilyl group is likewise removed by acidolysis, for example by a mineral acid, preferably hydrofluoric acid, or a strong carboxylic acid.

2-Halo-lower alkoxycarbonyl is removed using the above-mentioned reducing agents, for example a reducing metal, such as zinc, reducing metal salts, such as chromium(II) salts, or using sulfur compounds, for example sodium dithionite or preferably sodium sulfide and carbon disulfide.

When several protected functional groups are present, if desired the protecting groups can be so selected that more than one such group can be removed simultaneously, for example by acidolysis, such as by treatment with trifluoroacetic acid, or with hydrogen and a hydrogenation catalyst, such as a palladium-on-carbon catalyst. Conversely, the groups can also be so selected that they cannot all be removed simultaneously, but rather in a desired sequence, the corresponding intermediates being obtained.

Additional Process Steps

In the additional process steps, which are optional, functional groups of the starting compounds that are not intended to take part in the reaction may be unprotected or may be in protected form, for example they may be protected by one or more of the protecting groups mentioned above under Process a). The protecting groups may be retained in the end products or some or all of them may be removed in accordance with one of the methods mentioned under the heading "Removal of protecting groups".

Salts of compounds of formula I having a salt-forming group can be prepared in a manner known per se. For example, acid addition salts of compounds of formula I are obtained, for example, by treatment with an acid or a suitable anion exchange reagent Salts can be converted into the free compounds in customary manner; for example by treatment with a suitable basic agent.

Stereoisomeric mixtures, for example mixtures of diastereoisomers, can be separated into the corresponding isomers in a manner known per se by suitable separating procedures. For example, mixtures of diastereoisomers can be separated into the individual diastereoisomers by fractional crystallisation, chromatography, solvent partitioning and the like. Such separation can be carried out either at the stage of one of the starting materials or with the compounds of formula I themselves.

In a compound of formula I wherein $R_5$ is phenyl, that phenyl radical can be hydrogenated, for example by catalytic hydrogenation, especially in the presence of heavy metal oxides, such as rhodium/platinum mixed oxides, for example with the Nishimura catalyst, preferably in a polar solvent, such as an alcohol, for example methanol or ethanol, at temperatures of from 0° to 80° C., especially from 10° to 40° C., and at a preferred hydrogen pressure of from 1 to 10 atm, preferably at about normal pressure.

General process conditions

All the process steps given in this text can be carried out under reaction conditions known per se, but preferably under those specifically mentioned, in the absence or usually in the presence of solvents or diluents, preferably those solvents or diluents that are inert towards the reagents used and are solvents therefor, in the absence or presence of catalysts, condensation agents or neutralising agents, for example ion exchangers, such as cation exchangers, for example in the $H^+$ form, depending upon the nature of the reaction and/or the reactants at reduced, normal or elevated temperature, for example in a temperature range of from approximately −100° to approximately 190° C., preferably from approximately −80° to approximately 150° C., for example from −80° to −60° C., at room temperature, at from −20° to 40° C. or at the boiling point of the solvent used, under atmospheric pressure or in a closed vessel, optionally under pressure, and/or in an inert atmosphere, for example under an argon or nitrogen atmosphere.

In the case of all starting materials and intermediates, salts may be present when salt-forming groups are present. Salts may also be present during the reaction of such compounds, provided that the reaction will not be affected.

In all reaction steps, any isomeric mixtures that are formed can be separated into the individual isomers, for example diastereoisomers or enantiomers, or into any desired mixtures of isomers, for example racemates or diastereoisomeric mixtures, for example analogously to the methods described under the heading "Additional process steps".

In certain cases, for example in the case of hydrogenation, it is possible to carry out stereoselective reactions so that, for example, individual isomers may be obtained more easily.

The solvents from which those suitable for a particular reaction can be selected include, for example, water, esters, such as lower alkyl lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless the description of the processes indicates otherwise. Such solvent mixtures can also be used in working-up, for example by chromatography or partition.

The invention relates also to those forms of the process in which a compound obtainable as intermediate at any stage is used as starting material and the remaining steps are carried out or the process is interrupted at any stage or a starting material is formed under the reaction conditions or is used in the form of a reactive derivative or salt, or a compound obtainable in accordance with the process of the invention is produced under the process conditions and further processed in situ, it being preferable to use those starting materials which result in the compounds described above as being preferred, especially those described as being especially preferred, more especially preferred and/or very especially preferred.

The preparation of compounds of formula I is preferably carried out analogously to the processes and process steps given in the Examples.

The compounds of formula I, including their salts, may also be obtained in the form of hydrates, or their crystals may include, for example, the solvent used for crystallisation.

Pharmaceutical compositions:

The invention relates also to pharmaceutical compositions comprising compounds of formula I, and especially of formula Ia.

The pharmacologically acceptable compounds of the present invention may be used, for example, in the preparation of pharmaceutical compositions that comprise an effective amount of the active ingredient together or in admixture with a significant amount of inorganic or organic, solid or liquid, pharmaceutically acceptable carriers.

The invention relates also to a pharmaceutical composition suitable for administration to a warm-blooded animal, especially a human being, for the treatment or prevention of a disease that is responsive to inhibition of a retroviral protease, especially a retroviral aspartate protease, such as HIV-1 or HIV-II gag protease, for example a retroviral disease, such as AIDS or its preliminary stages, comprising a compound of formula I, or a pharmaceutically acceptable salt thereof, in an amount effective in the inhibition of the retroviral protease, together with at least one pharmaceutically acceptable carrier.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The invention relates also to a method of treating diseases caused by viruses, especially by retroviruses, especially AIDS or its preliminary stages, wherein a therapeutically effective amount of a compound of formula I according to the invention, or a pharmaceutically acceptable salt thereof, is administered especially to a warm-blooded animal, for example a human being, who on account of one of the mentioned diseases, especially AIDS or its preliminary stages, requires such treatment. The-dose to be administered to warm-blooded animals, for example human beings of approximately 70 kg body weight, is from approximately 3 mg to approximately 3 g, preferably from approximately 10 mg to approximately 1.5 g, for example approximately from 50 mg to 1000 mg per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90%, active ingredient Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, for example mannitol, for such solutions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid, or corresponding unsaturated acids, for example oleic acid, elaidic acid, erucic acid, brassidic acid or linoleic acid, if desired with the addition of antioxidants, for-example vitamin E, β-carotene or 3,5-di-tert-butyl-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, soybean oil and more especially groundnut oil and sesame oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for the active ingredients to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate.

Capsules are hard gelatin capsules made of gelatin and also soft, sealed capsules made of gelatin and a plasticiser, such as glycerol or sorbitol. The hard gelatin capsules may comprise the active ingredient in the form of granules, for example with fillers, such as lactose, binders, such as starches, and/or glidants, such as talc or magnesium stearate, and if desired with stabilisers. In capsules the active ingredient is preferably dissolved or suspended in suitable oily excipients, such as fatty oils, paraffin oil or liquid polyethylene glycols, it likewise being possible for stabilisers and/or antibacterial agents to be added.

There may be mentioned as such oils especially liquid fatty acid esters that contain as acid component a long-chained fatty acid, for example having from 8 to 22, especially from 12 to 22, carbon atoms, for example lauric acid, tridecylic acid, myristic acid, pentadecylic acid, palmitic acid, margaric acid, stearic acid, arachidic acid, behenic acid, or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially ethylene or propylene glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, groundnut oil, soybean oil and more especially sesame oil. Paraffin oil is also possible. Stabilisers, such as emulsifiers, wetting agents or surfactants, binders, such as starch pastes using, for example, corn, wheat, rice or potato starch, gelatin, tragacanth, methylcellulose, hydroxypropylmethyl-cellulose (preferred), sodium carboxymethylcellulose, cyclodextrin(s) and/or polyvinylpyrrolidone, and/or antibacterial agents may be added. Suitable emulsifiers are especially oleic acid, non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid-polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyoxyethylene glycol (300 or 400) stearate, polyethylene glycol 2000 stearate, especially ethylene oxide/propylene oxide block polymers of the ®Pluronic type (Wyandotte Chem. Corp.; trade mark of BASF, FRG) or ®Synperonic type (ICI). For example, if the active ingredient is not soluble in the mentioned oils it is present in the form of a suspension, for example having a particle size of approximately from 1 to 100 mm.

Colourings or pigments may be added to the tablets or dragée coatings or to capsule walls, for example for identification purposes or to indicate different doses of active ingredient Starting materials:

The present invention relates also to novel starting materials and/or intermediates and to processes for their preparation. The starting materials used and the reaction conditions selected are preferably those which result in the compounds described as being preferred.

In the preparation of all starting materials, free functional groups that are not intended to participate in the reaction in question may be unprotected or may be in protected form, for example they may be protected by the protecting groups mentioned above under Process a). Those protecting groups can be removed at suitable times by the reactions described under the heading "Removal of protecting groups".

The starting materials of Process a) are known or, if novel, can be prepared in accordance with processes known per se; for example the compounds of formula III can be prepared from hydrazine or suitable derivatives thereof, and the compounds of formula IV can be prepared from suitable amino acids or analogues thereof, for example having one of the mentioned side chains $R_5$.

The compounds of formula III can be obtained, for example, from compounds of formula

  (XI), which are known per se or can be prepared from hydrazine by the introduction of protecting groups as described under Process a) and in which $R_{11}$ is hydrogen or an amino-protecting group as described above under Process b), especially tert-lower alkoxycarbonyl, such as tert-butoxycarbonyl, aryl-lower alkoxycarbonyl, such as benzyloxycarbonyl or 9-fluorenylmethoxycarbonyl, or one of the abovementioned acyl amino-protecting groups, especially trifluoroacetyl, by alkylation with a compound of formula X as described above under Process e), or by reaction of the radical of sub-formula

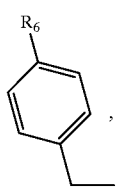  (A)

wherein $R_6$ is as defined for compounds of formula I, by reaction of a suitable carbonyl compound of formula X*, or a reactive derivative thereof, both as defined under Process f), with the free amino group of the compound of formula XI or an acylated derivative thereof and subsequent reduction of the resulting hydrazone to form a hydrazine derivative of formula

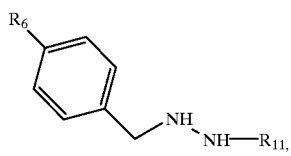  (XII)

the radicals in all the mentioned compounds being as defined above and functional groups in the reagents in question that are not to participate in the reaction being protected as necessary, and removal of the protecting group $R_{11}$ and by condensation under the conditions mentioned above under Process b) with an acid of formula VI, or an acid derivative thereof mentioned under Process b).

The carbonyl compounds of compounds X*, or reactive derivatives thereof, suitable for the introduction of the radical of sub-formula A that are used for the preparation of the compounds of formula XII, as defined above under Process f), are aldehydes or reactive derivatives thereof, the reactive carbonyl group of which, after the reaction with compounds of formula XI and the subsequent reduction, is a constituent of one of the mentioned radicals of sub-formula A, for example preferably 4-phenylbenzaldehyde or 4(2-cyanophenyl)benzaldehyde.

The reaction of the carbonyl compounds with the compounds of formula XI to form the corresponding hydrazones is carried out under conditions customarily used for the reaction of carbonyl compounds with amines, preferably in polar organic solvents, for example ethers, such as tetrahydrofuran or diethyl ether, alcohols, such as methanol or ethanol, carboxylic acid amides, such as dimethylformamide, or esters, such as ethyl acetate, or in aqueous solution, preferably in methanol, and also in the presence or absence of acid catalysts, for example carboxylic acids, such as formic acid or acetic acid, or sulfonic acids, such as p-toluenesulfonic acid, at temperatures of from 0° C. to the reflux temperature of the reaction mixture, preferably at temperatures of from 20° C. to the reflux temperature of the reaction mixture.

Compounds of formula

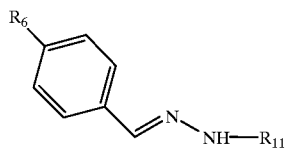

(XII*)

wherein $R_6$ and $R_{11}$ are as defined for compounds of formula XII are obtained.

The reduction of the resulting hydrazones of formula XII* is preferably carried out by hydrogenation in the presence of a suitable catalyst or with complex hydrides in the presence of acids. As catalysts suitable for hydrogenation there are used metals, such as nickel, iron, cobalt or ruthenium, or noble metals or oxides thereof, such as palladium or rhodium or oxides thereof, optionally, for example, applied to a suitable carrier, such as barium sulfate, aluminium oxide or carbon (active carbon) or in the form of skeleton catalysts, such as Raney nickel. Solvents customarily used for the catalytic hydrogenation are, for example, water, alcohols, such as methanol or ethanol, esters, such as ethyl acetate, ethers, such as dioxane, chlorinated hydrocarbons, such as dichloromethane, carboxylic acid amides, such as dimethylformamide, or carboxylic acids, such as glacial acetic acid, or mixtures of those solvents. The hydrogenation is carried out preferably at temperatures of from 10° to 250° C., especially from room temperature to 100° C., and preferably at hydrogen pressures of from 1 to 200 bar, especially from 1 to 10 bar, in the customary apparatus. For the reduction with complex hydrides, especially borohydrides, such as alkali metal cyanoborohydrides, for example sodium cyanoborohydride, it is preferable to use weak acids, such as sulfonic acids, for example p-toluenesulfonic acid, or carboxylic acids, such as acetic acid, preferably in alcohols, such as methanol or ethanol, or mixtures thereof with water (see, for example, Tetrahedron 49, 8605–8628 (1993)).

It is also possible for compounds of formula XI to be alkylated by reduction directly with compounds of formula X*, or reactive derivatives thereof, as defined under Process f), analogously to the conditions mentioned in Process f).

Also especially preferred for the preparation of compounds of formula XI are reaction conditions analogous to those described in J. Chem. Soc. Perkin 1, 1712 (1975).

Compounds of formula III can also be obtained, for example, by reacting a compound of formula XII*, as defined above, wherein $R_{11}$ is hydrogen (obtainable, for example, by the removal of protecting groups when $R_{11}$ is a protecting group), directly, with condensation under the conditions mentioned under Process b) above with acids of formula VI, or the acid derivatives thereof mentioned under Process b), to form compounds of formula

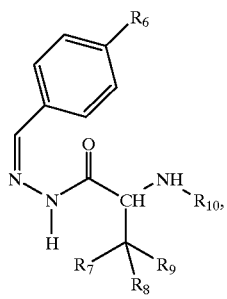

(III*)

wherein the radicals are as defined for compounds of formula I, which are then converted into compounds of formula III by reduction under conditions analogous to the conditions mentioned for the reduction of hydrazones of formula XII*.

Compounds of formula III* can also be obtained from the corresponding compounds of formula III', which are defined as described below, by reacting the latter With compounds of formula X*, as defined above, to form the hydrazones of formula III* under conditions analogous to those described above for the reaction of carbonyl compounds of formula X* with hydrazines of formula XI.

A compound of formula IV can be obtained, for example, by reduction of an amino acid of formula

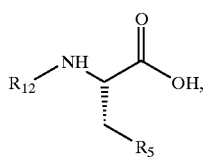

(XIII)

wherein $R_{12}$ is hydrogen or one of the amino-protecting groups mentioned under Process a), especially tert-lower alkoxycarbonyl, such as tert-butoxycarbonyl, aryl-lower alkoxycarbonyl, such as benzyloxycarbonyl or 9-fluorenylmethoxycarbonyl, or one of the acyl amino-protecting groups mentioned under Process a), especially trifluoroacetyl, and $R_5$ is as defined for compounds of formula I, to form an aldehyde of formula

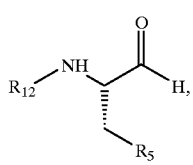

(XIV)

wherein the radicals are as last defined, subsequent reaction of that aldehyde with a ylide compound, preferably a sulfur ylide compound, to form an epoxide of formula

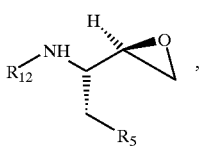

(XV)

wherein the radicals are as last defined, removal of the protecting group $R_{12}$ (the resulting free amino compound wherein $R_{12}$=hydrogen is stable, for example, in the form of an acid addition salt) and finally acylation of the amino group of the resulting compound with an acid of formula VIII wherein the radicals are as defined for formula VIII, under suitable conditions analogous to the conditions described for Process b).

The reduction of amino acids of formula XIII to the corresponding aldehydes of formula XIV is carried out, for example, by reduction to the corresponding alcohols and subsequent oxidation to the mentioned aldehydes.

The reduction to the alcohols (a free compound or (if necessary after the introduction of protecting groups, as described under Process a)) a compound N-protected by $R_{12}$, having the formula

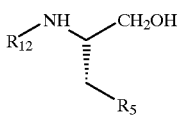

(XIII*)

wherein the radicals are as defined for compounds of formula XIII) is carried out, for example, by hydrogenation of the acid halides or other activated carboxylic acid derivatives mentioned under Process b) under the conditions mentioned for the hydrogenation of hydrazones obtained from compounds of formula XII or with complex hydrides, such as sodium borohydride. The subsequent oxidation of the resulting alcohols is possible, for example, by oxidation of the hydroxy group with a sulfoxide, such as dimethyl sulfoxide, in the presence of a reagent that activates the hydroxy group, such as a carboxylic acid chloride, for example oxalyl chloride, in inert solvents, for example a halogenated hydrocarbon, such as dichloromethane, and/or an acyclic or cyclic ether, such as tetrahydrofuran, at from $-80°$ to $0°$ C., for example from $-78°$ to $-50°$ C., or by oxidation, for example, with chromic acid or a derivative thereof, such as pyridinium chromate or tert-butyl chromate, dichromate/sulfuric acid, sulfur trioxide in the presence of heterocyclic bases, such as pyridine/$SO_3$, and also nitric acid, pyrolusite or selenium dioxide, in water, organic solvents, such as halogenated solvents, for example methylene chloride, carboxylic acid amides, such as dimethylformamide, or di-lower alkylsulfoxides, such as dimethyl sulfoxide, in the presence or absence of basic amines, for example tri-lower alkylamines, such as triethylamine, at temperatures of from $-50°$ to $100°$ C., preferably at from $-10°$ to $50°$ C., or by catalytic dehydrogenation, for example in the presence of metallic silver, copper, copper chromium oxide or zinc oxide at approximately from $200°$ to $400°$ C. (in the contact tube) with subsequent rapid cooling.

The direct reduction of the amino acids to the aldehydes is also possible, for example by hydrogenation in the presence of a partially poisoned palladium catalyst or by reduction of the corresponding amino acid esters, for example the lower alkyl esters, such as the ethyl ester, with complex hydrides, for example borohydrides, such as sodium borohydride, or preferably aluminium hydrides, for example lithium aluminium hydride, lithium tri(tert-butoxy) aluminium hydride or especially diisobutylaluminium hydride, in nonpolar solvents, for example in hydrocarbons or aromatic solvents, such as toluene, at from $-100°$ to $0°$ C., preferably from $-70°$ to $-30°$ C., and subsequent reaction to form the corresponding semicarbazones, for example with the corresponding acid salts of semicarbazones, such as semicarbazide hydrochloride, in aqueous solvent systems, such as alcohol/water, for example ethanol/water, at temperatures of from $-20°$ to $60°$ C., preferably from 10 to $30°$ C., and reaction of the resulting semicarbazone with a reactive aldehyde, for example formaldehyde, in an inert solvent, for example a polar organic solvent, for example a carboxylic acid amide, such as dimethylformamide, at temperatures of from $-30°$ to $60°$ C., preferably from $0°$ to $30°$ C., and then with an acid, for example a strong mineral acid, such as a hydrogen halide, in aqueous solution, optionally in the presence of the solvent used previously, at temperatures of from $-40°$ to $50°$ C., preferably from $-10°$ to $30°$ C. The corresponding esters are obtained by reaction of the amino acids with a corresponding alcohol, for example ethanol, analogously to the conditions employed in the condensation under Process b), for example by reaction with inorganic acid halides, such as thionyl chloride, in organic solvent mixtures, such as mixtures of aromatic and alcoholic solvents, for example toluene and ethanol, at temperatures of from $-50°$ to $50°$ C., preferably from $-10°$ to $20°$ C.

The preparation of the compounds of formula XIV is carried out in an especially preferred manner under conditions analogous to the reaction conditions mentioned in J. Org. Chem. 47, 3016 (1982) or J. Org. Chem. 43, 3624 (1978).

A sulfur ylide suitable for the conversion of compounds of formula XIV into the epoxides of formula XV is, for example, a dialkylsulfonium methylide, for example dimethylsulfonium methylide, an alkyl- or phenyl-dialkylaminosulfoxonium methylide, for example methyl- or phenyl-dimethylaminosulfoxonium methylide, or a dialkylsulfoxonium methylide, for example dimethyl- or diethyl-sulfoxonium methylide.

The sulfur ylide compound in question is advantageously prepared in situ from the corresponding sulfonium or sulfoxonium salt and a base, for example sodium hydride, in a dipolar aprotic solvent, for example dimethyl sulfoxide, or an ether, for example tetrahydrofuran or 1,2-dimethoxyethane, and is then reacted with the compound of formula XIV. The reaction is normally carried out at room temperature, with cooling, for example down to $-20°$ C., or with gentle heating, for example up to $40°$ C. The sulfide, sulfinamide or sulfoxide formed at the same time is removed in the subsequent aqueous working-up.

The reaction with a sulfur ylide is effected in an especially preferred manner analogously to the conditions mentioned in J. Org. Chem. 50, 4615 (1985).

A compound of formula XV can also be obtained from a compound of formula XIV, as defined above, by reaction thereof with a tri-lower alkylsilyl methyl Grignard compound, for example prepared from the corresponding halomethylsilane, such as chloromethyl-trimethylsilane, in an inert solvent, for example an ether, such as dioxane or diethyl ether, at temperatures of from $0°$ to $50°$ C., for example from room temperature to approximately $40°$ C., subsequent elimination with removal of the silyl radical and formation of a double bond, for example by means of a Lewis acid, such as $BF_3$, any amino-protecting group $R_{12}$ preferably also being removed, in an inert solvent, for example an ether, such as diethyl ether, or a halogenated hydrocarbon, such as dichloromethane, or a mixture thereof, at temperatures of from −50° C. to the reflux temperature, especially from 0° to 30° C., if necessary acylation again with the introduction of an amino-protecting group $R_{12}$, as defined above, and oxidation of the resulting double bond to form the oxirane, preferably with a percarboxylic acid, for example m-chloroperbenzoic acid or monoperphthalic acid (for example in magnesium salt form), in an inert solvent, for example a halogenated hydrocarbon; such as dichloromethane, or alcohols, such as methanol, lower alkanoylnitriles, such as acetonitrile water or mixtures thereof, at temperatures of from −20° C. to the reflux temperature of the mixture, for example at from 10° to 50° C.

Compounds of formula IV are preferably prepared by starting directly with an alcohol of formula XIII*, as defined above, which is also commercially available, reacting that alcohol with an acid of formula VIII, or with a reactive derivative thereof, as defined for Process c), under the conditions mentioned therein, with, if necessary, protecting groups being introduced, as described under Process a), and removed at suitable times, as described under the heading "Removal of protecting groups", there being obtained a compound analogous to the compound of formula XIII* wherein the place of $R_{12}$ is taken by the corresponding acyl radical from the acid of formula VIII; the resulting compound is oxidised under conditions analogous to those mentioned for the oxidation of alcohols of formula XIII* to form the corresponding aldehyde of formula

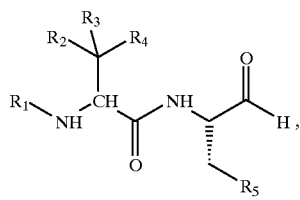

(XIV*)

wherein the radicals are as defined, and that aldehyde is then converted, for example with an ylide compound, as described for the conversion of compounds of formula XIV into compounds of formula XV, into the compound of formula IV.

The starting materials of Processes b), c) and d) are known or, if novel, can be prepared in accordance with processes known per se: for example a compound of formula V can be prepared from a suitable hydrazine derivative of formula XII wherein $R_{11}$ is a protecting group and the remaining radicals are as defined for compounds of formula V and a suitable epoxide of formula IV wherein the radicals are as defined for compounds of formula I (Process b); a compound of formula VII can be prepared from a suitable hydrazine derivative of formula III wherein the radicals are as defined for compounds of formula I and a suitable epoxide of formula XV wherein $R_{12}$ is a protecting group and the remaining radicals are as defined for compounds of formula I (Process c); and the compound of formula IX can be prepared from a suitable hydrazine derivative of formula XII wherein $R_{11}$ is hydrogen and the remaining radicals are as defined for compounds of formula I and a suitable epoxide of formula XV wherein $R_{12}$ is a protecting group and the remaining radicals are as defined for compounds of formula I (Process d), analogously to Process a), optionally using and removing protecting groups, as described under Process a) and under the heading "Removal of protecting groups", the protecting groups $R_{11}$ and $R_{12}$ preferably being as defined above in the definition of compounds of formula XI and XIII, respectively.

Compounds of formula I' wherein the substituents are as defined above can be prepared, for example, from compounds of formula III'

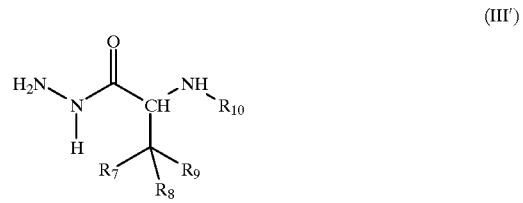

(III')

wherein the radicals are as defined for compounds of formula I, in a manner analogous to that described for Process b), by reaction with a compound of formula IV, wherein any functional groups present that are not to participate in the reaction may be protected as described in Process b) and freed again after the reaction.

Compounds of formula III' can be obtained from compounds of formula XI, as defined above, by reaction of an acid of formula VI, or a reactive acid derivative thereof, wherein the radicals are as defined above, in a manner analogous to that described for the reaction of compounds of formula XII with an acid of formula VI, and subsequent removal of the protecting group $R_{11}$ in accordance with one of the methods described under the heading "Removal of protecting groups".

Intermediates to which the invention relates are especially (a) compounds of formula IX wherein $R_5$ is cyclohexyl or especially phenyl and $R_6$ is cyanophenyl or phenyl, preferably 2-cyanophenyl or especially phenyl;

(b) compounds of formula III wherein $R_6$ is cyanophenyl or phenyl, preferably 2-cyanophenyl or especially phenyl, $R_7$, $R_8$ and $R_9$ are each lower alkyl, especially methyl, and $R_{10}$ is lower alkoxycarbonyl, especially methoxycarbonyl;

(c) compounds of formula IV wherein $R_1$ is lower alkoxycarbonyl, especially methoxycarbonyl, $R_2$, $R_3$ and $R_4$ are each lower alkyl, especially methyl, and $R_5$ is cyclohexyl or especially phenyl;

(d) compounds of formula V wherein $R_1$ is lower alkoxycarbonyl, especially methoxycarbonyl, $R_2$, $R_3$ and $R_4$ are each lower alkyl, especially methyl, $R_5$ is cyclohexyl or especially phenyl and $R_6$ is cyanophenyl or phenyl, preferably 2-cyanophenyl or especially phenyl; and/or (e) compounds of formula VII wherein $R_5$ is cyclohexyl or especially phenyl, $R_6$ is cyano phenyl or phenyl, preferably 2-cyanophenyl or especially phenyl, $R_7$, $R_8$ and $R_9$ are each lower alkyl, especially methyl, and $R_{10}$ is lower alkoxycarbonyl, especially methoxycarbonyl, or in each case a pharmaceutically acceptable salt thereof where at least one salt-forming group is present or (except in the case of compounds of formula IV) derivatives thereof having amino-protecting groups.

Where two amino-protecting groups are present they may be identical or different The amino-protecting groups used are, for example, the amino-protecting groups mentioned above under Process a). Preference is given to the corresponding compounds wherein the protecting groups are selected from those described as being preferred for $R_{11}$ and $R_{12}$ in compounds of formulae XI and XIII, respectively.

The preparation of the protected compounds of formula I is carried out, for example, in accordance with any one of the processes mentioned hereinbefore, especially from compounds of formulae III and IV wherein functional groups may be protected by protecting groups, as described under Process a).

The acids of formulae VI, VIII and VIIIa and the compounds of formula X, and the aldehydes suitable for the introduction of the radical of sub-formula A that are used for the preparation of the compounds of formula XII are known or, if novel, can be prepared in accordance with processes known per se.

The preparation of the acids of formula VI is effected by reaction of derivatives of lower alkoxycarboxylic acids suitable for the introduction of lower alkoxycarbonyl radicals, for example by reaction with the corresponding pyrocarbonic acid di-lower alkyl esters (especially pyrocarbonic acid dimethyl ester; Aldrich, Buchs, Switzerland) or preferably haloformic acid lower alkyl esters, such as chloroformic acid lower alkyl esters (especially chloroformic acid methyl ester, Fluka, Buchs, Switzerland), with amino acids of the formula

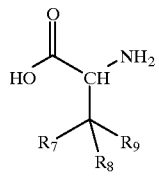

(XVI)

wherein the radicals $R_7$, $R_8$ and $R_9$ are as defined for compounds of formula VI, and are especially each methyl (or one is hydrogen and two are methyl), under conditions analogous to those described for acylation under Process b), especially in an aqueous alkali metal hydroxide solution, for example aqueous sodium hydroxide solution, in the presence of dioxane at temperatures of from 20 to 100° C., especially from 50 to 70° C.

Correspondingly, the compounds of formula VIII can be obtained from amino acids of formula

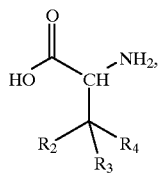

(XVII)

wherein $R_2$, $R_3$ and $R_4$ are as defined for compounds of formula I and especially one is hydrogen and two are methyl (or all three are methyl), and the compounds of formula VIIIa can be obtained from amino acids of formula

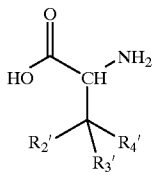

(XVIII)

wherein the radicals $R_2'$, $R_3'$ and $R_4'$ are each as defined for compounds of formula VIII'(lower alkyl, not hydrogen), by reaction with derivatives of the lower alkoxycarboxylic acid suitable for the introduction of lower alkoxycarbonyl radicals.

The amino acids of formulae XVI, XVII and XVIII are known or can be prepared in accordance with processes known per se. They are preferably in the (S)-form (in respect of the α-carbon atom).

Compounds of formula X can be prepared, for example, as follows:

The starting materials are compounds of formula

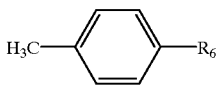

(XIX)

wherein $R_6$ is as defined for formula I. Those compounds can be obtained, for example, by the Ullmann biaryl synthesis method (see Chem. Rev. 38, 139 (1946) and 64, 613 (1964)) by copper-catalysed reaction of components of the compound of formula XIX each having a phenyl ring and having a halogen atom at the linkage site for the two phenyl rings, especially chlorine or bromine in one of the components to be coupled and iodine in the other; by way of the corresponding biphenylyloxazolines (see J. Am. Chem. Soc. 97, 7383 (1975) and cleavage thereof, for example by means of phosphorus oxychloride, to form the corresponding compounds wherein $R_6$ is cyanophenyl (especially 2-cyanophenyl) (see Tetrahedron Lett. (1983), 1437) or via Ni(O)-catalysed diaryl coupling (see J. Org. Chem. 42, 1821 (1977); see also J. Med. Chem. 34(8), 2525–2547 (1991)) (see especially the preparation of the compound having 3-cyanophenyl $R_6$ in accordance with J. Med. Chem. 34(8), 2525–2547 (1991) and with 4-cyanophenyl $R_6$ via p-bromobenzonitrile and p-$CH_3$-phenyl-ZnCl analogously to J. Org. Chem. 42(10), 1821 (1977)).

The methyl group can then be converted by free radical halogenation, for example with chlorine or bromine, especially by means of N-chloro- or N-bromo-amines, such as N-bromosuccinimide, preferably in a chlorinated hydrocarbon, such as methylene chloride or chloroform, optionally in the presence of catalytic amounts of an initiator for free radical reactions, for example a peroxide, such as dibenzoyl peroxide (e.g. 0.1–0.01, such as 0.07, equivalents) or of an azo compound, such as azobisisobutyronitrile, into the corresponding compound of formula X wherein X is halogen, especially chlorine or bromine. That compound can then (i) be converted by hydrolysis (for example in the presence of alkali hydroxide solutions, such as NaOH, often with phase transfer catalysis) into an alcohol of formula

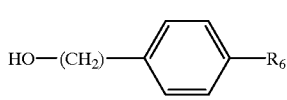
(Xa)

wherein $R_6$ is as defined for compounds of formula I, into which it is then possible to introduce other halogen radicals X by reaction with inorganic acid halides, such as thionyl or phosphoryl halides (for example the chlorides, bromides or iodides); or which can be converted by reaction with appropriate other organic or inorganic acids, such as strong organic sulfonic acids (for example used in the form of acid chlorides) into the other compounds of formula X; or they can (ii) be converted directly into other compounds of formula X by nucleophilic substitution in accordance with customary procedures with introduction of a different radical X.

The aldehydes of formula X* suitable for the introduction of the radical of sub-formula A that are used for the preparation of the compounds of formula XII can be obtained, for example, from the compounds of formula Xa, as defined above, by oxidation, for example with chromic acid or a derivative thereof, such as pyridinium chromate or tert-butyl chromate, dichromate/sulfuric acid, sulfur trioxide in the presence of heterocyclic bases, such as pyridine/SO$_3$, also nitric acid, pyrolusite or selenium dioxide, in water, organic solvents, such as halogenated solvents, for example methylene chloride, carboxylic acid amides, such as dimethylformamide, or di-lower alkyl sulfoxides, such as dimethyl sulfoxide, in the presence or absence of basic amines, for example tri-lower alkylamines, such as triethylamine, at temperatures of from −50° to 100° C., preferably at from −10° to 50° C.; by oxidation of the hydroxy group with a sulfoxide, such as dimethyl sulfoxide, in the presence of a reagent that activates the hydroxy group, such as oxalyl chloride, in inert solvents, for example a halogenated hydrocarbon, such as dichloromethane, and/or an acyclic or cyclic ether, such as tetrahydrofuran, at from −80° to −50° C.; or by catalytic dehydrogenation, for example in the presence of metallic silver, copper, copper chromium oxide or zinc oxide at approximately from 200° to 400° C. (in the contact tube) with subsequent rapid cooling; or they are commercially available or can be prepared in accordance with processes known per se, for example 4-phenylbenzaldehyde (Fluka, Buchs, Switzerland) or 4-(2-cyanophenyl)benzaldehyde (see Biomed. Chem. Lett. 3, 2667–2670 (1993) and J. Med. Chem. 34, 2525 (1991) cited therein). The corresponding reactive derivatives are prepared therefrom in accordance with procedures known per se (bisulfite addition compounds, for example, by reaction in aqueous concentrated sodium hydrogen sulfite solution; semi-acetals or acetals by reaction with the relevant alcohols, in the absence (semi-acetals) or presence of acids, such as ammonium chloride or hydrogen chloride (acetals); and thioacetals by reaction with corresponding mercaptans, also without acids).

Starting compounds of formula IX wherein the radicals $R_5$ and $R_6$ are as defined for compounds of formula I, or the precursors thereof protected at both nitrogen atoms which can be converted into the free compounds of formula IX by the removal of protecting groups in accordance with the methods described above under the heading "Removal of protecting groups", or salts of compounds of formula IX can be prepared also by reduction of an oxo compound of formula XX

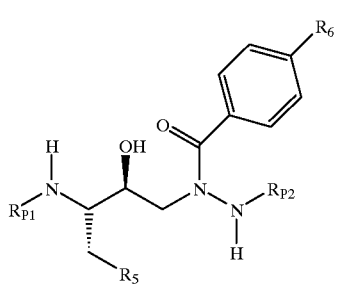
(XX)

wherein $R_{P1}$ and $R_{P2}$ are each an amino-protecting group or hydrogen and the other radicals are as defined for compounds of formula I;

that compound is in turn prepared by hydrogenation with a suitable complex hydride or with hydrogen in the presence of a suitable catalyst and acyl migration starting from a hydrazone of formula XXI

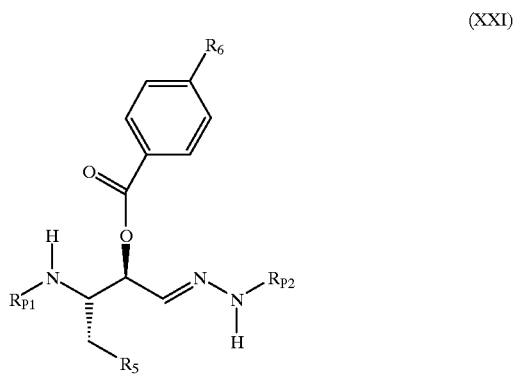
(XXI)

wherein the radicals are as defined for compounds of formula XX, which is in turn obtained preferably from a nitrile of formula XXII

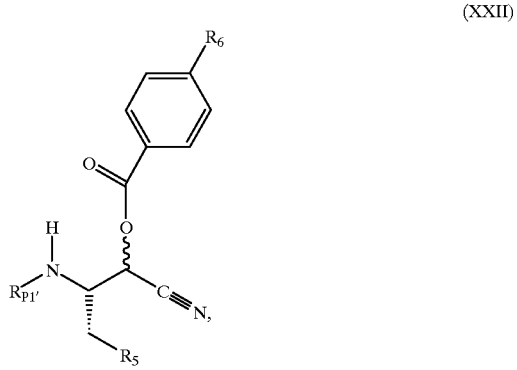
(XXII)

wherein $R_{P1}'$ is an amino-protecting group and $R_5$ and $R_6$ are as defined for compounds of formula I, by selective catalytic hydrogenation ((preferably) via an imino compound of formula XXIII

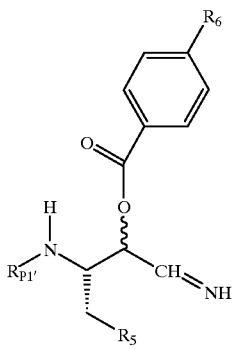

(XXIII)

wherein the radicals are as defined for compounds of formula XXII)
and reaction with a hydrazine derivative of formula XXIV

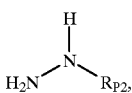

(XXIV)

wherein $R_{P2}$ is as defined for a compound of formula XX, and wherein further suitable protecting groups for functional groups may be present; the hydrazine derivative being added during the selective catalytic hydrogenation (or (further) being reacted with the resulting imino compound of formula XXIII only when the catalytic hydrogenation is complete), the compound of formula XXII being prepared preferably from an aldehyde of formula XXV

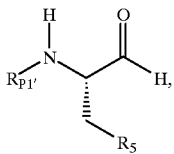

(XXV)

wherein $R_{P1}'$ is an amino-protecting group and $R_5$ has one of the meanings defined for compounds of formula I,
by reaction with a reactive derivative of a carboxylic acid of formula XXVI

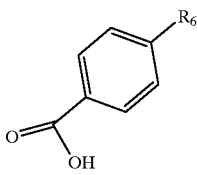

(XXVI)

wherein $R_6$ is as defined for compounds of formula I, in the presence of a cyanide salt;
the compounds of formulae XX to XXVI being in free form or, where salt-forming groups are present and the reaction conditions allow it, being used in the form of their salts.

A suitable amino-protecting group is especially an amino-protecting group that is not removed in any of the reductions and/or hydrogenations to be carried out in the reactions described hereinabove and hereinbelow. Also permissible, however, are protecting groups that are removable by those reductions, it being possible, if necessary, for fresh protecting groups to be introduced by conventional methods at each reaction step. Corresponding amino-protecting groups are defined under Process a) and are familiar to the person skilled in the art.

The reduction of an oxo compound of formula XX is preferably carried out using complex hydrides, such as borohydrides or metal hydrides, especially with borane/tetrahydrofuran ($BH_3$/THF) (especially preferred), borane/dimethyl sulfide ($BH_3/(CH_3)_2S$), tetra(n-butyl)ammonium borohydride (($CH_3-CH_2-CH_2-CH_2-$)$NBH_4$), trialkoxyborohydrides, such as tri-lower alkoxyborohydrides, alkali metal borohydrides, such as lithium, sodium or potassium borohydride, lithium triethylborohydride (Super-Hydride®), potassium tri(sec-butyl)borohydride (K-Selectride®), potassium tri(siamyl)borohydride (KS-Selectride®), lithium tri(sec-butyl)borohydride (L-Selectride®), lithium tri(siamyl)borohydride (LS-Selectride®), sodium tri(sec-butyl)borohydride (N-Selectride®), alkali metal aminoborohydrides or alkali metal (mono- or di-substituted amino)borohydrides, such as lithium aminoborohydride, sodium dimethylaminoborohydride, lithium diethylaminoborohydride, lithium di-n-propyl-amino borohydride, lithium diisopropylaminoborohydride, lithium-1-azaheptano-borohydride, lithium pyrrolidino-borohydride, lithium morpholino-borohydride, lithium piperidino-borohydride, lithium (N-ethyl-N-phenyl-amino) borohydride, sodium bis(2-methoxyethoxy)aluminium hydride (Vitride®), lithium aluminium hydride, lithium tri(methoxy)aluminium hydride, diisobutylaluminium hydride (Dibal) or lithium tri(tert-butoxy)aluminium hydride, in suitable solvents or solvent mixtures, especially ethers, such as tetrahydrofuran (especially preferred), di-lower alkyl ethers, such as diethyl ether or dioxane, or halogenated hydrocarbons, such as dichloromethane or chloroform, at preferred temperatures of from −10° to 80° C., especially from 0° to 60° C., for example from 0° C. to room temperature (for reagents and reaction conditions see also Heterocycles 14, 1437 (1980); Tetrahedron Lett. 33(32), 4533 (1992); U.S. Pat. No. 4,895,943; Synthet. Commun. 21, 1579 (1991); J. Chem. Soc. Perkin I, 1011 (1986); J. Org. Chem. 45, 1 (1980); or Bioorganic & Medicinal Chemistry Letters 4(16), 2055 (1994)).

When hydrogenation is carried out with a suitable complex hydride or with hydrogen in the presence of a suitable catalyst and acyl migration starting from a hydrazone of formula XXI, the procedure is preferably as follows:

First the hydrogenation is carried out.

As the complex hydride suitable for the hydrogenation there is used especially an alkali metal borohydride, such as an alkali metal cyanoborohydride, especially sodium cyanoborohydride ($NaBH_3CN$) in the presence of an acid, preferably a relatively strong acid, such as a mineral acid, for example sulfuric acid, phosphoric acid, hydrochloric acid, bromic acid or hydrofluoric acid, or especially an organic sulfonic acid, for example an alkanesulfonic acid, such as methanesulfonic acid, or an aromatic sulfonic acid, especially 4-toluenesulfonic acid, the reaction being carried out in suitable solvents, especially ethers, such as tetrahydrofuran or also dioxane, (see also Tetrahedron Lett. 49, 8605 (1993)), in the presence of water or in the absence thereof, at preferred temperatures of from 0° to 80° C., especially from 10° to 60° C., for example approximately at room temperature.

The hydrogenation with hydrogen in the presence of a suitable catalyst, especially nickel, rhodium, ruthenium, palladium and platinum catalysts, more especially Raney nickel or palladium or platinum catalysts, optionally on carriers, such as active carbon, aluminium oxide or barium sulfate, is preferably carried out at a hydrogen pressure of from 0.1 to 200 bar, preferably from 1 to 100 bar, and at preferred temperatures of from 20° to 120° C., especially from 40° to 100° C., preferably in the presence of organic solvents, such as alkanols, such as methanol, ethanol, isopropanol, sec-butanol or tert-butanol, ethers, such as diethyl ether, tetrahydrofuran or dioxane, amides, such as N,N-dimethylformamide or N,N-diethylformamide, aromatic hydrocarbons, such as toluene or xylene, aliphatic monocarboxylic acids, such as lower alkanoic acids, for example formic acid, acetic acid, propionic acid, butyric acid, isobutyric acid, iso- and n-valeric acid, or esters, such as alkyl esters of aliphatic monocarboxylic acids, for example formic acid methyl or ethyl ester, acetic acid methyl, ethyl, n-butyl or isobutyl ester, esters of carbonic acid, such as dimethyl or diethyl carbonate, or mixtures of the mentioned solvents, with special preference being given to acetic acid, methanol, ethanol, isopropanol, sec-butanol, tert-butanol or mixtures of those alcohols with ethyl acetate.

Hydrogenation with complex hydrides is preferred over hydrogenation with hydrogen in the presence of a suitable catalyst.

A borate complex is obtained which is either worked up and isolated, for example by partition, for example between an aqueous phase and an organic phase containing an ester, such as ethyl acetate, as solvent and (optionally after drying, for example over sodium sulfate) concentration by evaporation of the phase containing the borate complex, or is used directly in situ.

The subsequent acyl migration of the radical p-($R_6$)—$C_6H_5$—C(=O)— from the oxygen atom in formula XXI to the hydrazine nitrogen atom in formula XX is preferably effected under basic reaction conditions, especially in the presence of an aqueous base, especially an aqueous alkali metal hydroxide, such as potassium or sodium hydroxide, in the absence or presence of further solvents, such as ethers, preferably dioxane or di-lower alkoxy-lower alkanes, such as 1,2-dimethoxyethane, at preferred temperatures of from −10° to 60° C., especially from 0° to 30° C., and results in a corresponding compound of formula XX.

The selective catalytic hydrogenation of the nitrile group in a compound of formula XXII is preferably carried out directly in the presence of the hydrazine derivative of formula XXIV and without isolation of the imino compound of formula XXI using types of catalyst known per se, especially cobalt, nickel and noble metal catalysts, such as platinum, rhodium, palladium and ruthenium catalysts, which are used in free form or bonded to carriers, such as active carbon, aluminium oxide or barium sulfate, with special preference being given to rhodium on carriers, such as active carbon or aluminium oxide, or especially Raney nickel; in the presence of hydrogen, preferably molecular hydrogen; an acid, it being possible to use an inorganic or organic acid, especially an inorganic protonic acid, such as a hydrohalic acid, for example HCl, HBr and HF, phosphoric acid or sulfuric acid, or an organic protonic acid, for example a sulfinic acid, such as benzenesulfinic acid, an aliphatic and unsubstituted or substituted aromatic sulfonic acid, such as methanesulfonic acid, benzenesulfonic acid, p-toluenesulfonic acid, naphthalenesulfonic acid or naphthalenedisulfonic acid, an aliphatic monocarboxylic acid having preferably from 1 to 18 carbon atoms, such as formic acid, acetic acid, propionic acid, butyric acid, lauric acid, palmitic acid, stearic acid, a halogenated aliphatic monocarboxylic acid, such as chloroacetic acid, dichloroacetic acid, trichloroacetic acid or trifluoroacetic acid, an aliphatic dicarboxylic acid having preferably from 2 to 12 carbon atoms, such as oxalic acid, malonic acid, succinic acid, adipic acid or sebacic acid, an unsubstituted or substituted aromatic mono- or di-carboxylic acid, such as benzoic acid, toluic acid, naphthoic acid, phthalic acid or terephthalic acid; preferably a weak acid, such as aliphatic monocarboxylic acids having from 1 to 4 carbon atoms, such as formic acid, propionic acid, butyric acid or especially acetic acid; the acid and the hydrazine derivative of formula XXIV advantageously being used in an at least equimolar amount, based on the compound of formula XXII, and the hydrazine derivative preferably being used in an equimolar to twice the molar amount and the acid in equimolar to four times the molar amount, and it being possible, where appropriate, for excess acid to be used directly as solvent; in the presence or absence of an organic or aqueous organic solvent or solvent mixture, especially in the presence of alcohols, for example lower alkanols, such as methanol, ethanol, n-propanol, isopropanol, butanol or pentanol, or aliphatic or cyclic ethers, such as diethyl ether, di-n-propyl ether, diisopropyl ether, tetrahydropyran, tetrahydrofuran or dioxane; or cyclic or aliphatic amides, such as N-methyl-2-pyrrolidone, N-acetyl-2-pyrrolidone, formamide, N,N-dialkylamides of aliphatic monocarboxylic acids having from 1 to 3 carbon atoms in the acid moiety, such as N,N-dimethylformamide, N,N-dimethylacetamide and N,N-diethylacetamide, and/or mixtures of the mentioned solvents with water, with special preference being given to reaction in a $C_1$–$C_4$alkanol, especially methanol or ethanol, or in mixtures thereof with water; at preferred temperatures of from 0° to 150° C., especially from 20° to 60° C.; under normal pressure or under elevated pressure, preferably from normal pressure to a pressure of up to 10 bar, preferably up to 4 bar.

Alternatively it is also possible first to carry out the hydrogenation to an imino compound of formula XXIII which, without being isolated or after being fully or partially isolated, is then reacted with the hydrazine derivative of formula XXIV, the reaction conditions preferably corresponding to those last mentioned.

For the reaction with a reactive derivative of a carboxylic acid of formula XXVI there is used as reactive derivative especially a compound of formula XXVII

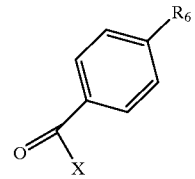

(XXVII)

wherein $R_6$ is as defined for compounds of formula I and wherein X is halogen, especially chlorine, or a radical of an acid bonded via an oxygen atom, especially a corresponding carboxylic acid, for example an acyloxy radical of the carboxylic acid of formula IX itself [radical p-($R_6$)—$C_6H_5$—C(=O)—O— (symmetric anhydride)] or especially lower alkanoyloxy, such as acetyloxy, or lower alkoxycarbonyloxy, such as isobutyloxycarbonyloxy; as cyanide salt there is preferably used an alkali metal cyanide, especially potassium or sodium cyanide; the reaction is preferably carried out under phase transfer conditions in the presence of a quaternary ammonium salt, especially tricaprylmethylammonium halide, such as tricaprylmethylammonium chloride (Aliquat), tetraalkylammonium halide, such as tetrabutylammonium chloride, trialkyl-aryl-lower alkylammonium halide, such as triethylbenzylammonium chloride, benzylcinchoninium halide, such as benzylcinchoninium chloride, benzylcinchonidinium halide, such as benzylcinchonidinium chloride, or benzylquininium halide, such as benzylquhininium chloride, in a suitable aqueous solvent mixture, such as a mixture of halogenated hydrocarbons with water, especially methylene chloride/water, 1,1-dichloroethane/water or chloroform/water, or mixtures of aliphatic ethers with water, such as dialkyl ether/water, for example diethyl ether/water, or cyclic ether/water, such as tetrahydrofuran/water or dioxane/water (phase separation especially in the case of a high salt concentration). The reaction takes place at preferred temperatures of from −20° to 50° C., especially from approximately 0° C. to room temperature.

The reaction to form a compound of formula XXII starting from a reactive acid derivative of a compound of formula XXVI and an aldehyde of formula XXV is preferably carried out stereoselectively, so that the molar ratio of the resulting compound of formula XXII wherein the asymmetric carbon atom carrying the cyano group is in the (R)-configuration to that wherein the asymmetric carbon atom carrying the cyano group is in the (S)-configuration is greater than approximately 3:1 and is especially from 4:1 to 10:1.

Alternatively it is also possible for the reaction of an aldehyde of formula XXV with hydrocyanic acid in the presence of the enzyme (S)-oxynitrilase, which can be obtained from almonds, either in the presence of almonds or almond extracts or of the purified (S)-oxynitrilase itself, or preferably in the presence of the enzyme (R)-oxynitrilase from Sorghum bicolor; which can be used in the form of cells, cell extracts or in purified form, in organic solvents, to be carried out stereoselectively, followed by acylation with an acid of formula XXVI or a reactive acid derivative thereof, as described above (see Tetrahedron Asymmetry 7(3), 663–666 (1996)).

Starting materials can also be prepared by the processes mentioned in EP 0 521 827 or obtained from the sources mentioned therein.

The preparation of starting materials for the preparation of compounds of formula I is preferably carried out analogously to the processes and process steps mentioned in the Examples.

EXAMPLES

The following Examples serve to illustrate the invention but do not limit the scope thereof Temperatures are given in degrees Celsius (° C.). Where no temperature is specified, the reactions that follow are carried out at room temperature. The $R_f$ values, which indicate the ratio of the seepage propagation of the substance in question to the seepage propagation of the eluant front, are determined on thin-layer silica gel plates (Merck, Darmstadt, Germany) by thin-layer chromatography (TLC) using the solvent systems indicated.

The quantitative ratio of solvents to one another is always given in parts by volume (v/v). The quantitative ratios given in the definition of the eluant systems for column chromatography are also in parts by volume.

The names customarily used in peptide chemistry are used to denote bivalent radicals of natural α-amino acids. The radical "tert-leucyl" is the radical of tert-leucine (α-tert-butylglycine). The configuration at the α-carbon atom, where known, is indicated by the prefix (L)- or (D)-.

Other abbreviations used:

| | |
|---|---|
| Anal. | elementary analysis |
| atm | physical atmospheres - pressure unit |
| | 1 atm corresponds to 1.013 bar |
| basic alox | basic aluminium oxide |
| brine | saturated sodium chloride solution |
| calc. | calculated |
| $CDCl_3$ | deuterochloroform |
| DMF | dimethylformamide |
| DMSO-$d_6$ | hexadeutero-dimethyl sulfoxide |
| EtOH | ethanol |
| FAB-MS | fast atom bombardment mass spectroscopy |
| h | hour(s) |
| MeOH | methanol |
| min | minute(s) |
| m.p. | melting point |
| $^1$H-NMR | proton-magnetic nuclear resonance |
| $R_f$ | ratio seepage propagation/eluant front in TLC |
| sat. | saturated |
| ThF | tetrahydrofuran |
| TLC | thin-layer chromatography (on silica gel 60 plates, Merck, Darmstadt) |

Example 1
1-(4-Biphenylyl)-2-N-(N-methoxycarbonyl-(L)-tert-leucyl)-amino-4(S)-hydroxy-5(S)-N-(N-methoxycarbonyl-(L)-valyl)-amino-6-phenyl-2-azahexane A solution of 56.4 g (95.3 mmol) of 1-(4-biphenylyl)-2-amino-4(S)-hydroxy-5(S)-N-(N-methoxycarbonyl)-(L)-valyl)-amino-6-phenyl-2-azahexane (Example 1f and 31.4 ml of N-methylmorpholine (Fluka, Buchs, Switzerland) in 650 ml of DMF is added dropwise over a period of 20 minutes to a solution of 18.04 g (95.3 mmol) of N-(methoxycarbonyl)-(L)-tert-leucine (Example 1g) and 28.4 g (95.3 mmol) of O-(1,2-dihydro-2-oxo-1-pyridyl)-N,N,N',N'-tetramethyluronium tetrafluoroborate (Fluka, Buchs, Switzerland) in 180 ml of DMF. The resulting mixture is stirred at room temperature for 16 hours and then poured into 7 liters of water. The suspension that immediately forms is filtered and the residue is washed with 1 liter of water. The crude product is dissolved in 2.5 liters of ethyl acetate, and the organic phase is washed with water (2×) and brine (1×), dried over magnesium sulfate and concentrated to a residual volume of about 1 liter. Crystallisation then begins and is completed by the addition of 2 liters of hexane at 5° C. The crystal mass is filtered off and washed with hexane; it yields, after drying at 40° C., a slightly yellowish product For further purification, the product is dissolved in 1 liter of hot MeOH (65° C.) and again concentrated by evaporation to a residual volume of about 200 ml in order to initiate crystallisation. The heterogeneous mixture is stirred at 0° C. for 6 hours. The crystals are then filtered off, washed with ice-cold methanol and dried at 45° C. in vacuo for 24 hours, yielding the title compound in the form of a white solid: m.p. 206–207° C.; $^1$H-NMR (CDCl$_3$) δ=7.6–7.15 (m, 14H); 6.75 (s, br, 1H); 6.51 (d, J=10, 1H); 5.28 (d, J=9, 1H); 5.13 (d, J=9, 1H); 4.87 (s, br, 1H); 4.18–3.85 (m, 4H); 3.65 (s, 3H); 3.60 (s, 3H); 3.6 (m, 2H); 2.95 (d, J=8, 2H); 2.83 (d, J=12, 1H); 2.60 (dd, J=12, 3, 1H); 1.98 (m, 1H); 0.78 (s, 9H), 0.82 and 0.78 (2d, J=7, 6H). FAB-MS (M+H)$^+$=690. Anal ($C_{38}H_{51}N_5O_7$·0.2 $H_2O$) C: calc. 65.82, found 65.98; H: calc. 7.47, found 7.49; N: calc. 10.10, found 10.12. TLC $R_f$(ethyl acetate)=0.61.

The starting materials are prepared as follows:

1a) N'-(Tert-butoxycarbonyl)-N²-(4-biphenylylmethyl)-hydrazone 75.8 g (0.416 mol) of 4-biphenylcarbaldehyde (=4-phenylbenzaldehyde; Aldrich, Buchs, Switzerland) are added at room temperature to a solution of 50 g (0.378 mol) of N-(tert-butoxycarbonyl)-hydrazine (=tert-butyl carbazate, Aldrich, Buchs, Switzerland) in 750 ml of absolute EtOH. When the addition is complete, the reaction mixture is heated under reflux for 16 hours. Then approximately 200 ml of solvent are distilled off. The remainder of the reaction mixture is diluted with 500 ml of water, whereupon the product begins to crystallise. Cooling to 0° C. completes the crystallisation, and the solid is isolated by filtration, washed with 1 liter of water and dried at 60° C., yielding the title compound: m.p. 188–189° C. ¹H-NMR (CD$_3$OD) δ=7.92 (s, 1H); 7.78 and 7.65 (AB system, J=8, 4H); 7.63 (m, 2H); 7.5–7.3 (m, 3H); 1.52 (s, 9H).

1b) N'-(Tert-butoxycarbonyl)-N²-(4-biphenylylmethyl)-hydrazine 9.4 g of 5% palladium on carbon are added to a solution of 94.4 g (0.318 mol) of the title compound from Example 1a) (hydrazone) in 2.5 liters of MeOH and the mixture is hydrogenated for 2 hours at room temperature and 1 atm hydrogen pressure. After the theoretical amount of hydrogen has been absorbed, the catalyst is filtered off and the filtrate is concentrated by evaporation. The residue is digested with 1 liter of hexane and yields the title compound in the form of a solid. Further title compound can be obtained by leaving the hexane solution to stand for several days: m.p. 84–85° C. ¹H-NMR (CD$_3$OD) δ=7.55 (m, 4H); 7.50–7.38 (m, 5H); 3.95 (s, 2H); 1.45 (s, 9H).

1c) 1-(4-Biphenylyl)-2-N-(tert-butoxycarbonyl)-amino-4(S)-hydroxy-5(S)-N-(trifluoroacetyl)-amino-6-phenyl-2-azahexane A solution of 46 g (154.3 mmol) of the title compound from Example 1b) (hydrazine) and 40 g (154.3 mmol) of 2(S)-N-(trifluoroacetyl)amino-1-phenyl-3(R)-3,4-epoxybutane (prepared according to EP 0 521 827, Example 16d) in 800 ml of absolute isopropanol is heated under reflux for 16 hours. 500 ml of isopropanol are then removed by distillation and the reaction mixture that remains is cooled to 0° C., whereupon the title compound begins to crystallise. The solid is filtered off and washed twice with 500 ml of isopropanol. For the purpose of further purification, the crude product so obtained is digested with 1 liter of hexane, separated from the hexane and dissolved in methylene chloride. After the methylene chloride solution has been completely concentrated by evaporation, the title compound is obtained in the form of a white solid. M.p. 189–190° C. ¹H-NMR (CD$_3$OD) δ=7.55–7.10 (m, 14H), 4.25 (m, 1H), 3.88–3.72 (m, 3H), 3.05–2.70 (m, 4H), 1.31 (s, 9H). Anal. (C$_{30}$H$_{34}$N$_3$O$_4$F$_3$) C: calc. 64.62, found 64.49; H: calc. 6.15, found 6.15; N: calc. 7.54, found 7.46.

1d) 1-(4-Biphenylyl)-2-N-(tert-butoxycarbonyl)-amino-4(S)-hydroxy-5(S)-amino-6-phenyl-2-azahexane 484 ml of a 1M aqueous solution of potassium carbonate are added dropwise at reflux temperature (64° C.) to a solutuion of 54 g (96.8 mmol) of the title compound from Example 1c) in 1.5 ml of MeOH. After 2.5 hours the reaction is complete, whereupon the majority of the MeOH is distilled off under reduced pressure. The reaction mixture, which is then heterogeneous, is diluted with 2 liters of ethyl acetate and 500 ml of water. The organic phase is washed once with 1 liter of brine, dried over magnesium sulfate and completely concentrated by evaporation. Drying yields the title compound in the form of a white solid. M.p. 134–136° C. ¹H-NMR (CD$_3$OD) δ=7.60–7.15 (m, 14H); 3.98–3.75 (m, 2H); 3.55 (m, 1H), 3.0–2.55 (m, 5H); 1.30 (s, 9H). Anal. (C$_{28}$H$_{35}$N$_3$O$_3$) C: calc. 72.86; found 72.72; H: calc. 7.64, found 7.56; N: calc. 9.10, found 9.07.

1e) 1-(4Biphenylyl)-2-N-(tert-butoxycarbonyl)-amino-4(S)-hydroxy-5(S)-N-(N-methoxycarbonyl-(L)-valinyl)-amino-6phenyl-2-azahexane 77 ml (554 mmol) of triethylamine are added to a suspension of 25.9 g (148 mmol) of N-(methoxycarbonyl)-(L)-valine (for preparation see Chem. Lett, p. 705 (1980)), 53.1 g (277 mmol) of N-(3-dimethylaminopropyl)-N'-ethyl-carbodiimide (hydrochloride salt) (Fluka, Buchs, Switzerland) and 25 g (185 mmol) of 1-hydroxybenzotriazole hydrate in 800 ml of DMF. After 30 minutes a solution 42.6 g (92.2 mmol) of the title compound from Example 1d) is added dropwise over a period of 20 minutes and the reaction mixture is stirred at room temperature for 2 hours. The solvent is then distilled off under reduced pressure and the residue is partitioned between 2.5 liters of ethyl acetate and 1.8 liters of water. A further 200 ml of MeOH and 150 ml of triethylamine are needed to dissolve the solid completely. The organic phase is washed with water (3×), sat sodium hydrogen carbonate solution (2×), water (2×) and brine (2×), dried over sodium sulfate and concentrated by evaporation. In that way the title compound is obtained in the form of a white solid. M.p. 191–192° C. Anal. (C$_{37}$H$_{49}$N$_5$O$_7$·0.3 H$_2$O) C: calc. 67.29, found 67.26; H: calc. 7.46, found 7.53; N: calc. 8.97, found 8.94.

1f) 1-(4-Biphenylyl)-2-amino-4(8)-hydroxy-5(S)-N-(N-methoxycarbonyl-(L)-valyl)-amino-6-phenyl-2-azahexane 57.2 g (92.4 mmol) of the title compound from Example 1e) are dissolved in a mixture of 200 ml of 4N hydrochloric acid in dioxane and 20 ml of MeOH and left at room temperature. According to TLC (19:1 chloroform:MeOH, v:v) the reaction is complete after 3 hours. The reaction solution is concentrated by evaporation and the residue is again dissolved in 250 ml of dioxane. After lyophilisation, the title compound is obtained in the form of an amorphous white solid. ¹H-NMR (CD$_3$OD) δ=7.7–7.15 (m, 14H); 4.17 (s, br, 2H); 3.95 (s, br, 1H), 3.75–3.55 (m, 2H); 3.63 (s, 3H); 3.05–2.70 (m, 4H), 1.85 (m, 1H); 0.75 and 0.72 (2d, J=7, 6H). FAB-MS (M+H)$^+$=519. TLC R$_f$ (12:1 methylene chloride:MeOH, v:v)=0.50.

1g) N-(Methoxycarbonyl)-(L)-tert-leucine 23.5 ml (305 mmol) of chloroformic acid methyl ester (Fluka, Buchs, Switzerland) are added over a period of 20 minutes to a solution of 20 g (152 mmol) of (L)-tert-leucine (=2(S)-amino-3,3-dimethyl-butyric acid=L-α-tert-butylglycine; Fluka, Buchs, Switzerland) in a mixture of 252 ml (504 mmol) of 2N aqueous sodium hydroxide solution and 80 ml of dioxane and the reaction solution is heated at 60° C. for 14 hours. After the reaction solution has cooled to room temperature, it is washed twice with methylene chloride. The aqueous phase is acidified to pH 2 with 4N aqueous hydrochloric acid and extracted three times with ethyl acetate. The organic extracts are combined, dried over sodium sulfate and concentrated by evaporation, the product beginning to solidify. Digestion of the solidified solid with hexane yields the title compound in the form of a white powder. M.p. 106–108° C. ¹H-NMR (CD$_3$OD) δ=4.0 (m, 1H); 3.65 (s, 3H); 1.01 (s, 9H). Anal. (C$_8$H$_{15}$NO$_4$·0.02 H$_2$O) C: calc. 50.69, found 50.69; H: calc. 8.00, found 7.95; N: calc. 7.39, found 7.35.

The following compounds are prepared in a manner analogous to that described in this Application text:

Example 2

1-(4-Biphenylyl)-2-N-(N-methoxycarbonyl-(L)-valinyl)-amino-4(S)-hydroxy-5(S)-N-(N-methoxycarbonyl-(L)-tert-leucyl)-amino-6-phenyl-2-azahexane The compound is prepared analogously to Example 1 from 1-(4-biphenylyl)-2-amino-4(S)-hydroxy-5(S)-N-(N-methoxycarbonyl-(L)-tert-leucyl)-amino-6-phenyl-2-azahexane and N-(methoxycarbonyl)-(L)-valine (preparation: see Chem. Lett, p. 705 (1980)). $^1$H-NMR (CD$_3$OD) δ=7.6–7.1 (m, 14H); 4.15 (t, br, J=8, 1H); 4.0 and 3.95 (AB system, J=12, 2H); 3.88 (s, 1H); 3.75 (m, 1H); 3.65 (s, 3H); 3.61 (s, 3H); 3.0–2.55 (m, 4H); 2.70 (m, 1H); 0.83 (s, 9H); 0.64 and 0.60 (2s, 6H). FAB-MS (M+H)$^+$=690. TLC R$_f$ (30:1 methylene chloride:methanol, v:v)=0.48.

The starting materials are prepared as follows:

2a) 1-(4-Biphenylyl)-2-amino-4(S)-hydroxy-5(S)-N-(N-methoxycarbonyl-(L)-tert-leucyl)-amino-6-phenyl-2-azahexane The compound is prepared analogously to Example 1f) starting from 1-(4-biphenylyl)-2-N-(tert-butoxycarbonyl)-amino-4(S)-hydroxy-5(S)-N-(N-methoxycarbonyl-(L)-tert-leucyl)-amino-6-phenyl-2-azahexane. $^1$H-NMR (CD$_3$OD) δ=7.6–7.15 (m, 14H); 4.2 (br, 3H); 3.95+3.65 (2s, br, 2H); 3.70–3.60 (m, 2H); 3.65 (s, 3H); 3.0–2.7 (m, 4H); 0.80 (s, 9H). FAB-MS (M+H)$^+$=533. TLC R$_f$ (19:1 methylene chloride:methanol, v:v)=0.50.

2b) 1-(4-Biphenylyl)-2-N-(tert-butoxycarbonyl)-amino-4(S)-hydroxy-5(S)-N-(N-methoxycarbonyl-(L)-tert-leucyl)-amino-6-phenyl-2-azahexane The compound is prepared analogously to Example 1e) using N-methoxycarbonyl-(L)-leucine (Example 1g) instead of N-methoxycarbonyl-(L)-valine. $^1$H-NMR (CD$_3$OD) δ=7.6–7.15 (m, 14H); 4.05 (m, 1H); 3.86 (s, 2H); 3.70 (m, 2H); 3.65 (s, 3H); 3.0–2.55 (m, 4H); 1.32 (s, 9H); 0.85 (s, 9H). FAB-MS (M+H)$^+$=633. TLC R$_f$ (19:1 methylene chloride:methanol, v:v)=0.57.

Example 3

1-[4-(2-Cyanophenyl)phenyl]-2-N-(N-methoxycarbonyl-(L)-valyl)-amino-4(S)-hydroxy-5(S)-N-(N-methoxycarbonyl-(L)-tert-leucyl)-amino-6-phenyl-2-azahexane With ice-cooling, 0.33 ml (2 mmol) of diethylphosphoryl cyanide and 1.12 ml (8 mmol) of triethylamine are squirted into a solution of 630 mg (1 mmol) of 1-[4-(2-cyanophenyl)phenyl]-2-amino-4(S)-hydroxy-5(S)-N-(N-methoxycarbonyl-(L)-tert-leucyl)-amino-6-phenyl-2-azahexane and 210 mg (1.2 mmol) of N-(methoxycarbonyl)-(L)-valine (preparation: see Chem. Lett. p.705 (1980)) in 8 ml of DMF. The reaction mixture is left at room temperature for 24 hours, poured into water and ethyl acetate and the phases are separated. The organic phase is washed 1× with water, sat. hydrogen carbonate solution, water, 10% citric acid, water and brine. The crude product is purified by chromatography on silica gel with hexane:ethyl acetate 4:1 (v:v). The product fractions are completely concentrated by evaporation and the residue is digested with hexane and yields the title compound in the form of a white solid. FAB-MS (M+H)$^+$=715. Anal. (C$_{39}$H$_{50}$N$_6$O$_7$.0.3 H$_2$O) C: calc. 65.04; found 64.7; H: calc. 7.08; found 7.0; N: calc. 11.67; found 11.3. TLC R$_f$ (4:1 hexane:ethyl acetate, v:v)=0.58.

The starting materials are prepared as follows:

3a) 1-[4-(2-Cyanophenyl)phenyl]-2-amino-4(S)-hydroxy-5(S)-N-(N-methoxycarbonyl-(L)-tert-leucyl)-amino-6-phenyl-2-azahexane The compound is prepared analogously to Example 1f) starting from 1-[4-(2-cyanophenyl)phenyl]-2-(tert-butoxycarbonyl)-amino-4(S)-hydroxy-5(S)-N-(N-methoxycarbonyl-(L)-tert-leucyl)-amino-6-phenyl-2-azahexane. FAB-MS (M+H)$^+$=558. Anal. (C$_{32}$H$_{39}$N$_5$O$_4$Cl$_2$.1.02 H$_2$O) C: calc. 59.22; found 61.6; H: calc. 6.68; found 7.0; N: calc. 10.79; found 10.6. TLC R$_f$ (19:1 methylene chloride:methanol, v:v)=0.54.

3b) 1-[4-(2-Cyanophenyl)phenyl]-2-(tert-butoxycarbonyl)-amino-4(S)-hydroxy-5(S)-N-(N-methoxycarbonyl-(L)-tert-leucyl)-amino-6-phenyl-2-azahexane The compound is prepared analogously to Example 3) using N-methoxycarbonyl-(L)-tert-leucine (Example 1g) instead of N-methoxycarbonyl-(L)-valine from 1-[4-(2-cyanophenyl)phenyl]-2-(tert-butoxycarbonyl)-amino-4(S)-hydroxy-5(S)-amino-6-phenyl-2-azahexane. FAB-MS (M+H)$^+$=658. Anal. (C$_{37}$H$_{47}$N$_5$O$_6$.0.21 H$_2$O) C: calc. 67.17; found 66.4; H: calc. 7.22; found 7.3; N: calc. 10.59; found 10.2. TLC R$_f$ (3:1 hexane:ethyl acetate, v:v)=0.57.

3c) 1-[4-(2-Cyanophenyl)phenyl]-2-(tert-butoxycarbonyl)-amino-4(S)-hydroxy-5(S)-amino-6-phenyl-2-azahexane The compound is prepared analogously to Example 1d) from 1-[4-(2-cyanophenyl)phenyl]-2-(tert-butoxycarbonyl)-amino-4(S)-hydroxy-5(S)-N-(trifluoroacetyl)-amino-6-phenyl-2-azahexane. M.p. 136–138° C. FAB-MS (M+H)$^+$=487. Anal. (C$_{29}$H$_{34}$N$_4$O$_3$.0.13 H$_2$O) C: calc. 71.24; found 71.25; H: calc. 7.06; found 7.12; N: calc. 11.46; found 11.14. TLC R$_f$ (9:1 methylene chloride:methanol, v:v)=0.41.

3d) 1-[4-(2-Cyanophenyl)phenyl]-2-tert-butoxycarbonyl)-amino-4(8)-hydroxy-5(S)-N-(trifluoroacetyl)-amino-6-phenyl-2-azahexane The compound is prepared analogously to Example 1c) using N$^1$-(tert-butoxycarbonyl)-N$^2$-[4-(2-cyanophenyl)phenyl]-hydrazine. M.p. 148–150° C. FAB-MS (M+H)$^+$=583. Anal. (C$_{31}$H$_{33}$F$_3$N$_4$O$_4$) C: calc. 63.91; found 63.46; H: 9H). 5.71; found 5.70; N: calc. 9.62; found 9.38. F: calc. 9.78; found 9.84. TLC R$_f$ (1:1 hexane:ethyl acetate, v:v)=0.68.

3e) N$^1$-(Tert-butoxycarbonyl)-N$^2$-[4-(2-cyanophenyl)phenyl]-hydrazine

The compound is prepared analogously to Example 1b) from N$^1$-(tert-butoxycarbonyl)-N$^2$-[4-(2-cyanophenyl)phenyl]-hydrazone. $^1$H-NMR (CDCl$_3$) δ=7.76 (d, J=7, 1H); 7.68–7.38 (m, 7H), 6.12 (s, br, 1H); 4.05 (s, 2H); 0.95 (s, 9H). FAB-MS (M+H)$^+$=324. TLC R$_f$ (1:1 hexane:ethyl acetate, v:v)=0.52.

3f) N$^1$-(tert-butoxycarbonyl)-N$^2$-[4-(2-cyanophenyl)phenyl]-hydrazone

The compound is prepared analogously to Example a) using 4-(2-cyanophenyl)-benzaldehyde (preparation: see BioMed. Chem. Lett. 3(12), p.2667 (1993); J. Med. Chem. 34, p. 2525 (1991)). $^1$H-NMR (CDCl$_3$) δ=7.93 (s, br, 1H); 7.88 (s, br, 1H); 7.79 (d, J=8, 2H); 7.75 (d, J=8, 1H); 7.63 (td, J=8 and 1, 1H); 7.57 (d, J=9, 2H); 7.52 (dd, J=8 and <1, 1H); 7.43 (td, J=8 and <1, 1H); 1.51 (s, 9H). FAB-MS (M+H)$^+$=322. Anal. (C$_{19}$H$_{19}$N$_3$O$_2$) C: calc. 71.01; found 70.1; H: calc. 5.96; found 6.1; N: calc. 13.07; found 12.8. TLC R$_f$ (3:1 hexane:ethyl acetate, v:v)=0.24.

Example 4

1-[4-(2-Cyanophenyl)phenyl]-2-N-(N-methoxycarbonyl-(L)-tert-leucyl)-amino-4(S)-hydroxy-5(S)-N-(N-methoxycarbonyl-(L)-valyl)-amino-6-phenyl-2-azahexane The compound is prepared analogously to Example 3) from 1-[4-(2-cyanophenyl)phenyl]-2-amino-4(8)-hydroxy-5

(S)-N-(N-methoxycarbonyl-(L)-valyl)-amino-6-phenyl-2-azahexane and N-(methoxycarbonyl)-(L)-tert-leucine (Example 1g). $^1$H-NMR (CD$_3$OD) δ=7.82 (d, J=8, 1H); 7.72 (td,J=8 and <1, 1H); 7.55–7.45 (m, 6H); 7.25–7.2 (m, 4H); 7.13 (m, 1H); 4.15 (t, br, J=7, 1H); 4.08 and 3.96 (AB system, J==12, 2H); 3.80 (d, br, J=7, 1H); 3.75 (br, 1H); 3.67 (br, 1H); 3.63 (s, 3H); 3.60 (s, 3H); 2.95 (m, 1H); 2.86 (m, 2H); 2.7 (d, br, J=12, 1H); 1.87 (m, 1H); 0.78 (m, 6H); 0.70 (s, 9H). FAB-MS (M+H)$^+$=715. TLC R$_f$ (ethyl acetate)= 0.71.

The starting materials are prepared as follows:

4a) 1-[4-(2-Cyanophenyl)phenyl]-2-amino-4(S)-hydroxy-5 (S)-N-(N-methoxycarbonyl-(L)-valyl)-amino-6-phenyl-2-azahexane The compound is prepared analogously to Example 1f) starting from 1-[4-(2-cyanophenyl)phenyl]-2-(tert-butoxycarbonyl)-amino-4(S)-hydroxy-5(S)-N-(N-methoxycarbonyl-(L)-valyl)-amino-6-phenyl-2-azahexane. FAB-MS (M+H)$^+$=544. Anal. (C$_{31}$H$_{37}$N$_5$O$_4$.0.99 HCl.1.29 H$_2$O) C: calc. 61.75; found 61.71; H: calc. 6.78; found 6.84; N: calc. 11.61; found 11.14; Cl found 6.07. TLC R$_f$ (9:1 methylene chloride:methanol, v:v)=0.72.

4b) 1-[4-(2-Cyanophenyl)phenyl]-2-(tert-butoxycarbonyl)-amino-4(S)-hydroxy-5(S)-N-(N-methoxycarbonyl-(L)-valyl)-amino-6-phenyl-2-azahexane The compound is prepared analogously to Example 3) starting from 1-[4-(2-cyanophenyl)phenyl]-2-(tert-butoxycarbonyl)-amino-4(S)-hydroxy-5(S)-amino-6-phenyl-2-azahexane (Example 3c) and N-methoxycarbonyl-(L)-valine. FAB-MS (M+H)$^+$=644. Anal. (C$_{36}$H$_{45}$N$_5$O$_6$) .0.19 H$_2$O) C: calc. 66.81; found 66.49; H: calc. 7.07; found 7.12; N: calc. 10.82; found 10.68. TLC R$_f$(1:1 hexane:ethyl acetate, v:v) 0.21.

Example 5

1-(4-Biphenylyl)-4(S)-hydroxy-5(S)-2,5-bis[N-(N-methoxycarbonyl-(L)-tert-leucyl)-amino]-6-phenyl-2-azahexane A solution of 161 mg (0.849 mmol) of N-(methoxycarbonyl)-(L)-tert-leucine (Example 1g) and 253 mg (0.849 mmol) of O-(1,2-dihydro-2-oxo-1-pyridyl)-N,N,N',N'-tetramethyluronium tetrafluoroborate (Fluka, Buchs, Switzerland) in 1.6 ml of DMF is stirred for 30 minutes and then a solution of 200 mg (0.425 mmol) of 1-(4-biphenylyl)-4(S)-hydroxy-5(S)-2,5-diamino-6-phenyl-2-azahexane hydrochloride and 280 μl (2.55 mmol) of N-methylmorpholine (Fluka, Buchs, Switzerland) in 2 ml of DMF is added. The mixture is stirred at room temperature for 62 hours and then poured into 40 ml of water. After 1 hour the resulting suspension is filtered. Chromatography (SiO$_2$; methylene chloride/methanol 30:1) of the residue and precipitation from methylene chloride with diisopropyl ether/hexane yield the title compound in the form of a white solid: FAB-MS (M+H)$^+$=704. Anal (C$_{39}$H$_{53}$N$_5$O$_7$.0.48 H$_2$O) C: calc. 65.56, found 65.60; H: calc. 7.89, found 7.60; N: calc. 9.80, found 9.64; H$_2$O: calc. 1.21, found 1.21. TLC R$_f$ (methylene chloride/methanol 30:1)=0.24.

The starting materials are prepared as follows:

5a) 1-(R)-Cyano-N-2-(S)-(tert-butyloxycarbonyl)amino-3-phenylpropyl-4-(phenyl)benzoate A solution of 8.34 g (128 mmol) of potassium cyanide is added dropwise at 0° C. to a solution of 12;46 g (50 mmol) of Boc-(L)-phenylalaninal, 13.00 g (60 mmol) of biphenylcarbonyl chloride (Aldrich, Buchs, Switzerland) and 924 mg (2.2 mmol) of N-benzylcinchoninium chloride in 200 ml of THF (filtered through basic alox) (dropwise addition time 20 min). After that time the cooling bath is removed and the reaction mixture is stirred at room temperature for 4 hours, then diluted with 200 ml each of ethyl acetate and water, and the phases are separated; the organic phase is washed with 0.1N hydrochloric acid and 10% hydrogen carbonate solution. The organic extracts are dried over sodium sulfate and concentrated by evaporation. The cyanohydrin ester is obtained in the form of an epimer mixture (1-(R)/1-(S)= 4.2:1). The analytical data come from a sample of the pure 1-(R)-epimer (title compound) crystallised from diisopropyl ether m.p. 118–120° C. $^1$H-NMR (CDCl$_3$) δ8.10–8.00 (m, 2H, 7.75–7.6 (m, 4H); 7.55–7.25 (m, 8H); 5.65 (d, J=4.8 Hz, 1H); 4.80 (d, J=9 Hz, 1H); 4.50 (m, 1H), 3.20 (dd, J=14.4, 8.2 Hz, 1H); 3.00 (dd, J=14.4, 8.2 Hz, 1H); 1.40 (s, 9H). FAB-MS (M+H)$^+$=457. Anal. (C$_{28}$H$_{28}$N$_2$O$_4$) C: calc. 73.66; found 73.52; H: calc. 6.18; found 6.06; N: calc. 6.14; found 6.14. TLC: R$_f$ (4:1 hexane:ethyl acetate) 0.39.

5b) N-1-(Tert-butyloxycarbonyl)-N-2-{3-(S)-3-[(tert-butyloxycarbonyl)amino]-2(R)-(4-biphenylyl)carbonyloxy-4-phenyl-butylidene}-hydrazone 2.4 ml (42 mmol) of acetic acid and 5.7 g (43 mmol) of tert-butyl carbazate are added to a solution of 19.75 g (40 mmol) of a (4.2:1) mixture of the cyanohydrin ester from Example 5a) in 400 ml of methanol and hydrogenation is carried out in the presence of 10 g of ethanol-moistened Raney nickel for 8 hours at room temperature and under 1 atm hydrogen pressure. The reaction mixture is diluted with methylene chloride and filtered over Celite® (trade mark of the Celite Corp; filter aid based on diatomaceous earth). The filtrate is concentrated by evaporation, dissolved again in methylene chloride and washed with 500 ml each of water and 10% hydrogen carbonate solution, dried over sodium sulfate and again concentrated to dryness by evaporation. The crude product is crystallised from acetonitrile and yields the title compound in the form of a diastereoisomerically pure hydrazone: m.p. 178–180° C. $^1$H-NMR (CDCl$_3$) δ8.12 (d, J=7.8 Hz, 2H); 7.82 (s, br,1H), 7.70–7.57 (m, 4H); 7.55–7.35 (m, 3H); 7.32–7.1 (m, 6H); 5.62 (t, br, J=5 Hz, 1H); 4.94 (d, br, J=8 Hz, 1H); 4.38 (m, br, 1H); 2.95 (m, 2H); 1.47 (s, 9H); 1.32 (s, 9H). FAB-MS (M+H)$^+$=574. Anal. (C$_{33}$H$_{39}$N$_3$O$_6$) C: calc. 69.09; found 69.13; H: calc. 6.85; found 6.75; N: calc. 7.32; found 7.42. TLC: R$_f$ (10:1 methylene chloride:THF) 0.65.

5c) 1-(4-Biphenylyl)-1-oxo-5-(S)-2,5-[di(tert-butyloxycarbonyl)]amino-4(S)-hydroxy-6-phenyl-2-azahexane 1.16 g (18.5 mmol) of sodium cyanoborohydride are added at room temperature to a suspension of 9.63 g (16.8 mmol) of hydrazone (title compound from Example 5b)) in 90 ml of THF (filtered over basic alox). A solution of 3.52 g (18.5 mmol) of 4-toluenesulfonic acid hydrate (Fluka, Buchs, Switzerland) in 34 ml of THF is added dropwise, with stirring at room temperature, to the reaction mixture (dropwise addition time 20 min). After a further 1.5 hours, for the purpose of working-up, the reaction mixture is diluted with 150 ml of ethyl acetate and washed with 150 ml each of sat sodium chloride solution 10% hydrogen carbonate solution and sat. sodium chloride solution. The organic phases are dried over sodium sulfate and concentrated by evaporation; they yield the corresponding borate complex in the form of a yellow oil. That oil is dissolved in 130 ml of dioxane, diluted with 80 ml of 1N sodium hydroxide solution at 0° C. and stirred at room temperature for 16 hours. The reaction mixture is then poured onto ice, neutralised with 79 ml of 1N hydrochloric acid and extracted three times using 100 ml of methylene chloride each time. The organic extracts are dried over sodium sulfate and concentrated by evaporation. The crude product is purified by chromatography (SiO$_2$; 2%→10% THF in methylene chloride) and yields the title compound in the form of a colourless amorphous solid which is digested in diisopropyl ether: m.p. 125–128° C. $^1$H-NMR (DMSO-d$_6$, 150° C.) δ8.66 (br, 1H), 7.62 (m, 4H); 7.58 (d, J=7.5 Hz, 2H); 7.45 (t, J=7.5 Hz, 2H); 7.38 (m, 1H); 7.26 (m, 4H); 7.17 (m, 1H); 5.72 (d, br, J=10 Hz,1H); 4.4 (br, 1H); 3.92 (br,1H); 3.83 (m,1H); 3.71 (m, 1H); 3.54 (d, br,1H); 2.92 (dd, J=14, 7 Hz, 1H); 2.80 (dd, J=14, 7 Hz, 1H); 1.32 (s, 9H); 1.29 (s, 9H). FAB-MS (M+H)+=576. Anal. (C$_{33}$H$_{41}$N$_3$O$_6$) C: calc. 68.85; found 68.88: H: calc. 7.18: found 7.19; N: calc. 7.30; found 7.31; TLC: R$_f$ (10:1 methylene chloride:THF) 0.58.

5d) 1-(4-Biphenylyl)-5(S)-2,5-[di(tert-butyloxycarbonyl) amino]-4(S)-hydroxy-6-phenyl-2-azahexane 10 ml (10 mmol) of borane/THF complex (1M in THF; Fluka, Buchs, Switzerland) are added at 0° C. to a solution of 1.02 g (1.77 mmol) of 1-(4-biphenylyl)-1-oxo-5-(S)-2,5-[di(tert-butyloxycarbonyl)]amino-4(S)-hydroxy-phenyl-2-azahexane in 10 ml of THF (filtered through basic alox). After 1.5 hours at that temperature, the cooling bath is removed and the reaction mixture is stirred at room temperature for 2.5 hours. The reaction mixture is then poured into 20 ml of 1N sodium hydroxide solution. When the vigorous evolution of gas has subsided, the mixture is diluted with water and extracted with 500 ml of methylene chloride. The organic phases are dried over sodium sulfate and concentrated. The crude product is purified by chromatography (SiO$_2$; methylene chloride/THF 49:1) and, after digestion in diisopropyl ether, yields the title compound: m.p. 185–186° C., $^1$H-NMR (DMSO-d$_6$, 150° C.) δ7.6 (m, 2H); 7.53 (m, 2H); 7.42 (m, 4H); 7.32 (m, 1H); 7.23–7.12 (m, 6H); 5.55 (d, br, J=10 Hz, 1H); 4.15 (d, J=4 Hz, 1H); 3.95 (s, 2H); 3.84 (m, 1H); 3.68 (m, 1H); 2.9–2.75 (m, 4H), 1.33 (s, 9H); 1.31 (s, 9H), FAB-MS (M+H)$^+$=562, Anal. (C$_{33}$H$_{43}$N$_3$O$_5$) C: calc. 70.56; found 70.16; H: calc. 7.72; found 7.80; N: calc. 7.48; found 7.24, TLC: R$_f$ (19:1 methylene chloride:THF) 0.66.

Alternative Variant to Example 5d)

Under a N$_2$ atmosphere, 2.1 ml (2.1 mmol) of a 1.00M solution of diisobutylaluminium hydride in methylene chloride are slowly added dropwise to an ice-cold solution of 200 mg (0.347 mmol) of 1-(4-biphenylyl)-1-oxo-5-(S)-2,5-[di (tert-butyloxycarbonyl)]-amino-4(S)-hydroxy-6-phenyl-2-azahexane in 5 ml of THF (foams). After 2 hours 7 ml of ethyl acetate and after a further 30 minutes 70 ml of methanol are added. The reaction mixture is heated to room temperature and stirred for 2 hours; 0.5 ml of water and 5 g of sodium sulfate are added and the mixture is stirred for a further 1 hour to complete the reaction. The salts are filtered off and the filtrate is concentrated by evaporation. Chromatography on silica gel (eluant 2:1 hexane/ethyl acetate) yields 1-(4-biphenylyl)-5(S)-2,5-[di(tert-butyloxycarbonyl)-amino]-4(S)-6-phenyl-2-azahexane (Example 8a) having the physical data given therein.

5e) 1-(-Biphenylyl)-4(S)-hydroxy-5(S)-2,5-diamino-6-phenyl-2-azahexane hydrochloride A solution of 300 mg (0.534 mmol) of 1-(4-biphenylyl)-5(S)-2,5-[di(tert-butyloxycarbonyl)-amino]-4(S)-hydroxy-6-phenyl-2-azahexane in 10 ml of 4N HCl/dioxane is stirred at room temperature for 90 minutes. Dilution with dioxane and lyophilisation yield the title compound which is used directly in Example 5.

Example 6

Gelatin Solution

A sterile-filtered aqueous solution, containing 20% cyclodextrins as solubiliser, of one of the compounds of formula I mentioned in the preceding Examples (e.g. the title compound from Example 1) as active ingredient, is so mixed, with heating and under aseptic conditions, with a sterile gelatin solution containing phenol as preservative that 1.0 ml of solution has the following composition:

| | |
|---|---|
| active ingredient | 3 mg |
| gelatin | 150 mg |
| phenol | 4.7 mg |
| dist. water containing 20% cyclodextrins as solubiliser | 1.0 ml |

Example 7

Sterile Dry Substance for Injection 5 mg of one of the compounds of formula I mentioned in the preceding Examples (for example the title compound from Example 1) as active ingredient are dissolved in 1 ml of an aqueous solution containing 20 mg of mannitol and 20% cyclodextrins as solubiliser. The solution is sterile-filtered and, under aseptic conditions, introduced into a 2 ml ampoule, deep-frozen and lyophilised. Before use, the lyophilisate is dissolved in 1 ml of distilled water or 1 ml of physiological saline. The solution is administered intramuscularly or intravenously. The formulation can also be introduced into double-chamber disposable syringes.

Example 8

Nasal Spray 500 mg of finely ground (<5.0 mm) powder of one of the compounds of formula I mentioned in the preceding Examples (for example the compound from Example 1) are suspended as active ingredient in a mixture of 3.5 ml of Myglyol 812® and 0.08 g of benzyl alcohol. The suspension is introduced into a container having a metering valve. 5.0 g of Freon 12® (dichlorodifluoromethane; trade mark of DuPont) are introduced under pressure through the valve into the container. The "Freon" is dissolved in the Myglyol/benzyl alcohol mixture by shaking. The spray container contains approximately 100 single doses which can be administered individually.

Example 9

Film-Coated Tablets

The following constituents are processed for the preparation of 10,000 tablets each comprising 100 mg of active ingredient:

| | |
|---|---|
| active ingredient | 1000 g |
| corn starch | 680 g |
| colloidal silicic acid | 200 g |
| magnesium stearate | 20 g |
| stearic acid | 50 g |
| sodium carboxymethyl starch | 250 g |
| water | quantum satis |

A mixture of one of the compounds of formula I mentioned in the preceding Examples (for example the compound from Example 1) as active ingredient, 50 g of corn starch and the colloidal silicic acid is processed with a starch paste made from 250 g of corn starch and 2.2 kg of demineralised water to form a moist mass. That mass is forced through a sieve of 3 mm mesh size and dried in a fluidised bed drier at 45° for 30 minutes. The dried granules are pressed through a sieve of 1 mm mesh size, mixed with a previously sieved mixture (1 mm sieve) of 330 g of corn starch, the magnesium stearate, the stearic acid and the sodium carboxymethyl starch and compressed to form slightly convex tablets.

Example 10

Capsules (I)

Crystalline 1-(4-biphenylyl)-2-N-(N-methoxycarbonyl-(L)-tert-leucyl)-amino-4(S)-hydroxy-5(S)-N-(N-methoxycarbonyl-(L)-valyl)-amino-6-phenyl-2-azahexane (active ingredient) is micronised using a customary knife mixer (e.g. Turmix) (particle size about 1 to 100 μm). ®Pluronic F 68 (block polymer of polyethylene and polypropylene glycol; Wyandotte Chem. Corp., Michigan, USA; also obtainable from Emkalyx, France; trade mark of BASF) is likewise micronised using a customary mixer and the fines content is removed using a sieve (0.5 mm) and used further as below. 16.00 g of sesame oil are placed in a glass beaker and 1.20 g of the micronised active ingredient, 1.20 g of the fines content of ®Pluronic F 68 and 1.20 g of hydroxypropylmethylcellulose (Cellulose HP-M-603 from Shin-Etsu Chemicals Ltd., Tokyo, JP) are added with stirring using a stirring device (IKA-Werk, FRG) combined with a toothed stirrer (diameter 46 mm) (stirring speed: 2000 rev/min). Twenty minutes' stirring at the speed indicated produces a suspension of pasty consistency which is introduced into hard gelatin capsules (20×40 mm; R. P. Scherer AG, Eberbach, FRG).

Example 11

Capsules (II)

For the preparation of 10,000 capsules comprising 100 mg of active ingredient 1-(4-biphenylyl)-2-N-(N-methoxycarbonyl-(L)-tert-leucyl)-amino-4(S)-hydroxy-5(S)-N-(N-methoxycarbonyl-(L)-valyl)-amino-phenyl-2-azahexane per capsule, the following constituents are processed as follows:

| | |
|---|---|
| active ingredient | 1000 g |
| ® Pluronic F 68 | 1000 g |
| hydroxypropylmethylcellulose | 1000 g |
| sesame oil | 1000 g |
| (for origin of constituents see Example 10) | |

The sesame oil is placed in a heatable vessel (Fryma) and the ®Pluronic F 68 is scattered in. The vessel is heated to 60° C. and the ®Pluronic F 68 is distributed with stirring (duration about 2 hours). With stirring and homogenisation, the mixture is cooled to about 30° C. The hydroxypropyl-methylcellulose and the active ingredient are scattered in and, with stirring and homogenisation (about 1 hour), distributed in the oil mass. The suspension of pasty consistency is introduced into hard gelatin capsules (size 0; obtainable, for example, from Elanco or Parke-Davies (Caprogel)) or soft gelatin capsules (20 mm oblong; R. P. Scherer AG, Eberbach, FRG) using customary apparatus.

Example 12

$IC_{50}$ Values in Respect of HIV-1-Protease

In the test system described above (with RRSNQVSQNYPIVQNIQGRR), SEQ ID NO:1 the following $IC_{50}$ values are obtained for Examples 1 to 5:

| Example | $IC_{50}$ (μM) |
|---|---|
| 1 | 0.051 |
| 2 | 0.085 |
| 3 | 0.038 |
| 4 | 0.043 |
| 5 | 0.058 |

Example 13

$ED_{90}$ Values in Respect of MT-2-Cells

In the test system described above (with HIV-1-infected MT-2-cells) the following $ED_{90}$ values are obtained for Examples 1 to 5:

| Example | $ED_{90}$ (μM) |
|---|---|
| 1 | 3 |
| 2 | 3 |
| 3 | 10 |
| 4 | 3 |
| 5 | 3 |

Example 14

Blood Levels in Mice after Oral Administration

In the test system described above (with BALB/c mice after peroral administration of 120 mg of active ingredient/kg) the following plasma levels are obtained:

| Example | plasma concentration (time after administration) | |
|---|---|---|
| | 30 min | 90 min |
| 1 | 6.33 | 5.35 |
| 2 | 0.64 | 1.11 |
| 3 | 1.42 | 1.95 |
| 4 | 1.68 | 1.93 |
| 5 | 5.53 | 4.91 |

What is claimed is:

1. A compound of formula I

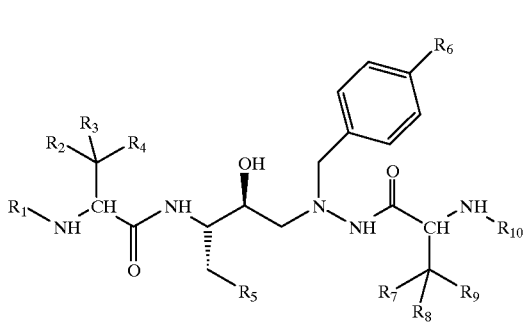

(I)

wherein
- $R_1$ and $R_{10}$ are each independently of the other lower alkoxycarbonyl;
- either $R_2$, $R_3$ and $R_4$ are each independently of the other $C_1$–$C_4$alkyl and $R_7$, $R_8$ and $R_9$ are each selected from hydrogen and $C_1$–$C_4$alkyl, with not more than 2 of the radicals being hydrogen;
- or $R_7$, $R_8$ and $R_9$ are each independently of the other $C_1$–$C_4$alkyl and $R_2$, $R_3$ and $R_4$ are each selected from hydrogen and $C_1$–$C_4$alkyl, with 1 or 2 of the radicals being hydrogen;
- $R_5$ is phenyl or cyclohexyl; and
- $R_6$ is phenyl or cyanophenyl;

or a salt thereof.

2. A compound of formula I according to claim 1, wherein
- $R_1$ and $R_{10}$ are each independently of the other lower alkoxycarbonyl;
- either $R_2$, $R_3$ and $R_4$ are each independently of the other $C_1$–$C_4$alkyl and $R_7$, $R_8$ and $R_9$ are each selected from hydrogen and $C_1$–$C_4$alkyl, but not more than one of the radicals may be hydrogen;
- or $R_7$, $R_8$ and $R_9$ are each independently of the other $C_1$–$C_4$alkyl and $R_2$, $R_3$ and $R_4$ are each selected from hydrogen and $C_1$–$C_4$alkyl, but not more than one of the radicals may be hydrogen;
- $R_5$ is phenyl or cyclohexyl; and
- $R_6$ is phenyl or cyanophenyl;

or a salt thereof.

3. A compound of formula I according to claim 1, wherein
- $R_1$ and $R_{10}$ are each independently of the other lower alkoxycarbonyl;
- $R_7$, $R_8$ and $R_9$ are each independently of the other $C_1$–$C_4$alkyl and $R_2$, $R_3$ and $R_4$ are each selected from hydrogen and $C_1$–$C_4$alkyl, but not more than one of the radicals may be hydrogen;
- $R_5$ is phenyl or cyclohexyl; and
- $R_6$ is phenyl or cyanophenyl;

or a salt thereof.

4. A compound of formula I wherein
- $R_1$ and $R_{10}$ are each independently of the other tert-butoxy-, ethoxy- or methoxy-carbonyl;
- either $R_2$, $R_3$ and $R_4$ are each independently of the other methyl and $R_7$, $R_8$ and $R_9$ are each selected from hydrogen and methyl, but not more than one of the radicals may be hydrogen;
- or $R_7$, $R_8$ and $R_9$ are each independently of the other methyl and $R_2$, $R_3$ and $R_4$ are each selected from hydrogen and methyl, but not more than one of the radicals may be hydrogen;
- $R_5$ is phenyl; and
- $R_6$ is phenyl or 2-cyanophenyl;

or a salt thereof.

5. A compound of formula I wherein
- $R_1$ and $R_{10}$ are each independently of the other tert-butoxy-, ethoxy- or methoxy-carbonyl;
- $R_7$, $R_8$ and $R_9$ are each independently of the other methyl and $R_2$, $R_3$ and $R_4$ are each selected from hydrogen and methyl, but not more than one of the radicals may be hydrogen;
- $R_5$ is phenyl; and
- $R_6$ is phenyl or 2-cyanophenyl;

or a salt thereof.

6. A compound of formula

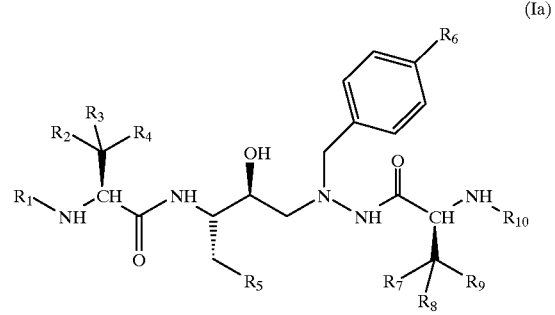

(Ia)

according to claim 1, wherein the radicals are as defined, or a salt thereof.

7. A compound of formula I according to claim 1, selected from the compounds having the names 1-(4-biphenylyl)-2-N-(N-methoxycarbonyl-(L)-valinyl)-amino-4(S)-hydroxy-5(S)-N-(N-methoxycarbonyl-(L)-tert-leucyl)-amino-6-phenyl-2-azahexane; and 1-[4-(2-cyanophenyl)phenyl]-2-N-(N-methoxycarbonyl-(L)-valyl)-amino-4(S)-hydroxy-5(S)-N-(N-methoxycarbonyl-(L)-tert-leucyl)-amino-6-phenyl-2-azahexane;

or a pharmaceutically acceptable salt thereof.

8. A compound according to claim 1 which is 1-(4-biphenylyl)-2-N-(N-methoxycarbonyl-(L)-tert-leucyl)-amino-4(S)-hydroxy-5(S)-N-(N-methoxycarbonyl-(L)-valyl)-amino-6-phenyl-2-azahexane, having the following structure,

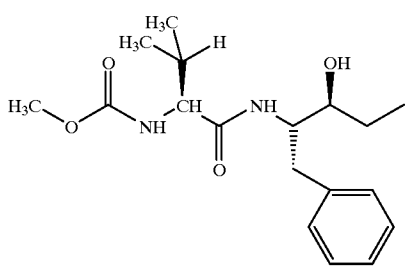

-continued

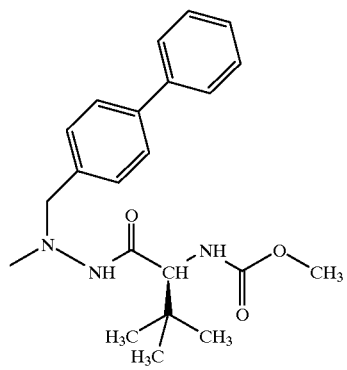

or a pharmaceutically acceptable salt thereof.

9. A compound of formula I according to claim 1 having the name 1-[4-(2-cyanophenyl)phenyl]-2-N-(N-methoxycarbonyl-(L)-tert-leucyl)-amino-4(S)-hydroxy-5(S)-N-(N-methoxycarbonyl-(L)-valyl)-amino-6-phenyl-2-azahexane, or a pharmaceutically acceptable salt thereof.

10. A compound of formula I according to claim 1 having the name 1-(4-biphenyl)-4(S)-hydroxy-5(S)-2,5-bis[N-(N-methoxycarbonyl-(L)-tert-leucyl)-amino]-6-phenyl-2-azahexane, or a pharmaceutically acceptable salt thereof.

11. A compound according to claim 1, or a pharmaceutically acceptable salt thereof, for use in a method for the treatment of the human or animal body.

12. A pharmaceutical composition comprising a compound of formula I according to claim 1, or a pharmaceutically acceptable salt of such a compound having at least one salt-forming group, together with a pharmaceutically acceptable carrier.

13. A method of treating diseases caused by retroviruses, wherein a therapeutically effective amount of a compound of formula I according to the invention, according to claim 1, or a pharmaceutically acceptable salt thereof, is administered to a warm-blooded animal requiring such treatment on account of one of the mentioned diseases.

14. A pharmaceutical composition suitable for administration to a warm-blooded animal for the treatment or prevention of a disease that is responsive to inhibition of a retroviral protease, comprising a compound of formula I, or a pharmaceutically acceptable salt thereof, according to claim 1 in an amount effective in the inhibition of the retroviral protease, together with at least one pharmaceutically acceptable carrier.

15. A process for the preparation of a compound of formula I according to claim 1, wherein a) a hydrazine derivative of formula

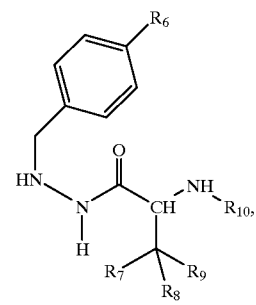

(III)

wherein the radicals $R_6$, $R_7$, $R_8$, $R_9$ and $R_{10}$ are as defined for compounds of formula I, is added to an epoxide of formula

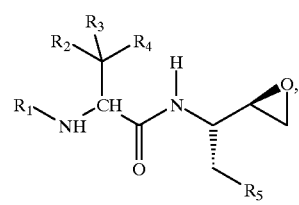

(IV)

wherein the radicals $R_1$, $R_2$, $R_3$, $R_4$ and $R_5$ are as defined for compounds of formula I, free functional groups with the exception of those participating in the reaction being, if necessary, in protected form, and any protecting groups are removed, or b) an amino compound of formula

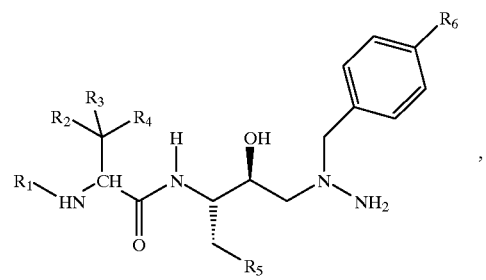

(V)

wherein the radicals $R_1$, $R_2$, $R_3$, $R_4$, $R_5$ and $R_6$ are as defined for compounds of formula I, is condensed with an acid of formula

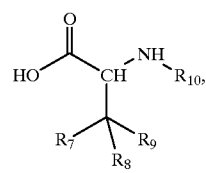

(VI)

or with a reactive acid derivative thereof, wherein the radicals $R_7$, $R_8$, $R_9$ and $R_{10}$ are as defined for compounds of formula I, free functional groups with the exception of those participating in the reaction being, if necessary, in protected form, and any protecting groups are removed, or c) an amino compound of formula

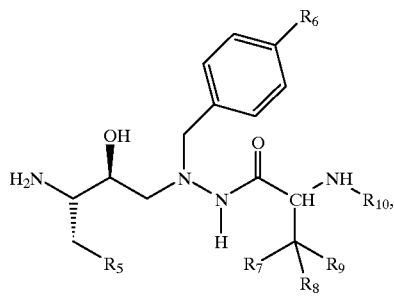

(VII)

wherein the radicals $R_5$, $R_6$, $R_7$, $R_8$, $R_9$ and $R_{10}$ are as defined for compounds of formula I, is condensed with an acid of formula

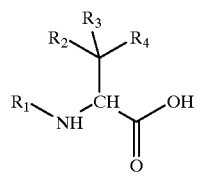

(VIII)

or with a reactive acid derivative thereof, wherein $R_1$, $R_2$, $R_3$ and $R_4$ are as defined for compounds of formula I, free functional groups with the exception of those participating in the reaction being, if necessary, in protected form, and any protecting groups are removed, or d) for the preparation of compounds of formula I wherein the substituent pairs $R_1$ and $R_{10}$, $R_2$ and $R_7$, $R_3$ and $R_8$ and $R_4$ and $R_9$ each represent two identical radicals, as defined for compounds of formula I, but none of the radicals $R_2$, $R_3$, $R_4$, $R_7$, $R_8$ and $R_9$ is hydrogen, and $R_5$ and $R_6$ are as defined for compounds of formula I, a diamino compound of formula

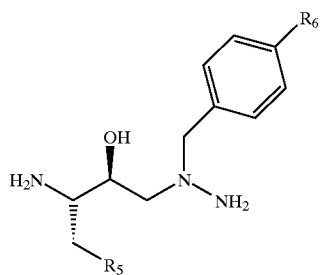

(IX)

wherein the radicals are as defined immediately above, is condensed with an acid of formula

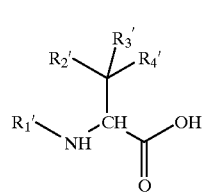

(VIIIa)

or with a reactive acid derivative thereof, wherein $R_1'$, $R_2'$, $R_3'$ and $R_4'$ are as defined for $R_1$ and $R_{10}$, $R_2$ and $R_7$, $R_3$ and $R_8$, and $R_4$ and $R_9$ in formula I, the pairs $R_1$ and $R_{10}$, $R_2$ and $R_7$, $R_3$ and $R_8$ and $R_4$ and $R_9$ each representing two identical radicals and none of the radicals $R_2$, $R_3$, $R_4$, $R_7$, $R_8$ and $R_9$ being hydrogen, and free functional groups with the exception of those participating in the reaction being, if necessary, in protected form, and any protecting groups are removed, or e) an imino compound of formula I'

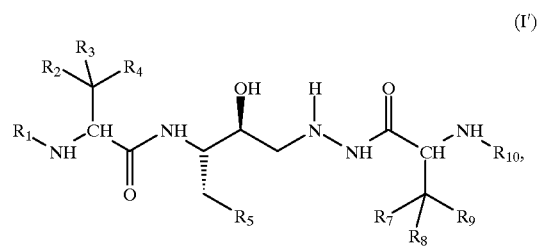

(I')

wherein the radicals $R_1$, $R_2$, $R_3$, $R_4$, $R_5$, $R_7$, $R_8$, $R_9$ and $R_{10}$ are as defined for compounds of formula I, is reacted with a compound of formula X

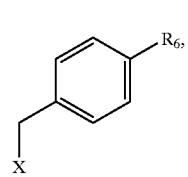

(X)

wherein X is a leaving group and $R_6$ is as defined for compounds of formula I, free functional groups with the exception of those participating in the reaction being, if necessary, in protected form, and any protecting groups are removed, or f) an imino compound of formula I'

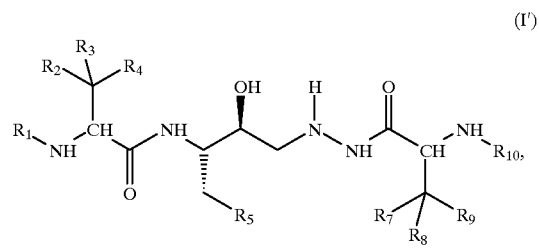

(I')

wherein the radicals $R_1$, $R_2$, $R_3$, $R_4$, $R_5$, $R_7$, $R_8$, $R_9$ and $R_{10}$ are as defined for compounds of formula I, is reacted, with reductive alkylation, with an aldehyde of formula X*

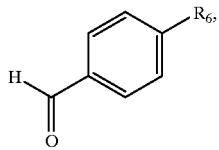

(X*)

wherein $R_6$ is as defined for compounds of formula I, or a reactive derivative thereof, free functional groups with the exception of those participating in the reaction being, if necessary, in protected form, and any protecting groups are removed, and, if desired, a compound of formula I having at least one salt-forming group obtainable in accordance with any one of processes a) to f) above is converted into a salt or an obtainable salt is converted into the free compound or into a different salt and/or isomeric mixtures which may be obtainable are separated and/or a compound of formula I according to the invention is converted into a different compound of formula I according to the invention.

* * * * *